(12) United States Patent
Andersson et al.

(10) Patent No.: US 7,947,235 B2
(45) Date of Patent: May 24, 2011

(54) MICROFLUIDIC DEVICE WITH FINGER VALVES

(75) Inventors: Per Andersson, Uppsala (SE); Gunnar Ekstrand, Uppsala (SE); Gerald Jesson, Enköping (SE)

(73) Assignee: Gyros AB, Uppsala (SE)

( * ) Notice: Subject to any disclaimer, the term of this patent is extended or adjusted under 35 U.S.C. 154(b) by 412 days.

(21) Appl. No.: 11/911,414

(22) PCT Filed: Apr. 13, 2006

(86) PCT No.: PCT/SE2006/000452
§ 371 (c)(1),
(2), (4) Date: May 8, 2008

(87) PCT Pub. No.: WO2006/110095
PCT Pub. Date: Oct. 19, 2006

(65) Prior Publication Data
US 2008/0226501 A1 Sep. 18, 2008

Related U.S. Application Data

(60) Provisional application No. 60/672,831, filed on Apr. 18, 2005, provisional application No. 60/671,130, filed on Apr. 14, 2005.

(30) Foreign Application Priority Data
Jul. 29, 2005 (SE) ........................................ 0501749

(51) Int. Cl.
*G01N 1/10* (2006.01)

(52) U.S. Cl. ....... 422/506; 422/68.1; 422/507; 422/533; 422/537; 422/548

(58) Field of Classification Search .................... None
See application file for complete search history.

(56) References Cited

U.S. PATENT DOCUMENTS

| 6,706,519 | B1 | 3/2004 | Kellogg et al. | |
|---|---|---|---|---|
| 6,911,183 | B1 | 6/2005 | Handique et al. | |
| 2001/0001060 | A1* | 5/2001 | Kellogg et al. | 435/7.1 |
| 2002/0003001 | A1* | 1/2002 | Weigl et al. | 137/806 |

(Continued)

FOREIGN PATENT DOCUMENTS
WO WO2004027391 * 4/2004

OTHER PUBLICATIONS

International Search Report issued Jul. 3, 2006 during the prosecution of International Application No. PCT/SE2006/000452.

*Primary Examiner* — In Suk Bullock
*Assistant Examiner* — Timothy G Kingan
(74) *Attorney, Agent, or Firm* — Fulbright & Jaworski L.L.P.

(57) ABSTRACT

A microfluidic device (1) comprising a hydrophilic microchannel structure (2) in which there is a functional unit that comprises a microconduit I (17) in which there is an inlet end (16), an outlet end (18), and a capillary stop function I (24) in the form of a local non-wettable surface area (44). The capillary stop function (24) defines a segment of microconduit I (17). Microconduit I (17) is within at least a part of this segment (46) divided into two or more microchannels (42). A part of the non-wettable surface area (44a,b) is associated with an inner wall of each of the microchannels (42).

21 Claims, 4 Drawing Sheets

U.S. PATENT DOCUMENTS

| | | |
|---|---|---|
| 2002/0075363 A1 | 6/2002 | McNeely et al. |
| 2002/0106786 A1 | 8/2002 | Carvalho et al. |
| 2002/0150512 A1 | 10/2002 | Kellogg et al. |
| 2003/0195106 A1 | 10/2003 | Kellogg et al. |
| 2004/0091399 A1* | 5/2004 | Chung et al. .................. 422/100 |
| 2004/0109793 A1 | 6/2004 | McNeely et al. |
| 2005/0153432 A1 | 7/2005 | Andersson et al. |
| 2006/0084174 A1* | 4/2006 | Ogawa et al. .................. 436/63 |

* cited by examiner

MICROFLUIDIC DEVICE WITH FINGER VALVES

The present invention is a U.S. §371 application that claims priority to PCT International Application No. PCT/SE2006/000452, filed Apr. 13, 2006, which claims priority to Swedish Application Serial No. 0501749-6, filed Jul. 29, 2005, and also claims priority to U.S. Provisional Patent Application Ser. No. 60/672,831, filed Apr. 18, 2005, and to U.S. Provisional Patent Application Ser. No. 60/671,130, filed Apr. 14, 2005, all of which applications are incorporated by reference herein in their entirety.

TECHNICAL FIELD

The present invention relates to a microfluidic device in which there are one or more hydrophilic microchannel structures each of which comprises one or more of the innovative microfluidic functionalities or units presented herein, and to fluidic methods or operations utilizing these functionalities or units.

A microfluidic device of the invention has one or more microchannel structures which each comprises at least one or more of the functional units of the invention:

A. Capillary valve unit that permits decreased spinning for downstream transport of an aliquot of a liquid, once the front of the liquid has passed the valve (kick-valve).
B. Capillary valve unit requiring maintained increased spinning in order for a front of a liquid to pass the capillary valve (upward-turn valve).
C. Capillary stop unit (finger valve and/or finger vent).
D. Protected capillary valve unit.
E. Unit for separating an upper phase, typically a liquid phase, from a denser phase typically comprising particulate material.
F. Detection unit.

All units A-F are primarily contemplated for centrifugal-based microfluidic devices. Units such as C, D, E, and F may also be used in systems in which liquid flow is driven by other forces including capillary forces.

If not otherwise apparent from the context, the terms "upper" and "higher" versus "lower", "upward" versus "downward", "inward" versus "outward", "above" versus "below" etc will refer to locations in relation to the direction of the main force used to drive liquid transport or flow downstream within the major parts of a microchannel structure, for instance within a major flow path. In centrifugal-based systems this means that a "higher" or an "upper" level/position (inner position) is at a shorter radial distance compared to a "lower" level/position (outer position). The radial distance of a level/position is the shortest way from the level/position concerned to a spin axis about which the device can be spun to create centrifugal force used in the device. Similarly, the terms "up", "upward", "inwards", and "down", "downwards", "outwards" etc will mean towards and from, respectively, the spin axis. A "height" will be considered as the difference in radial position or distance between two levels with the base level being the outer/lower level.

The terms discussed in the preceding paragraph are not to be mixed up with the terms "upstream" or "downstream" that solely refer to the order in which various functional units appear in a flow path and/or the order the various steps of a protocol are carried out. In other words downstream means "after" and upstream "before".

A hydrophilic microchannel structure comprises a system of one or more microconduits/microchannels and/or microcavities that are hydrophilic/wettable in the sense that once a liquid front of a liquid, primarily aqueous, has started to pass a valve function or an inlet opening within the structure, the liquid will further penetrate the system by self-suction or capillary force (passively) unless hindered by a valve function and/or vent or by a counter-pressure, for instance created by air in a non-vented interior area, or by other means. The hydrophilicity downstream a valve function is typically such that passive liquid transport can be resumed, if desired, after the liquid front has passed the valve. The principle of self-suction in particular applies to the innovative units described herein and to structures/units that are in a dry state. The microchannel structure may also contain microconduits/microchannels that are not intended for liquid transport. These latter microconduits/microchannels are typically hydrophobic at least at their connection to a hydrophilic part of the structure that is intended for transport of liquid.

That two parts of a microchannel structure is in fluid or liquid communication with each other means that liquid is intended to be transported between them.

All patent and patent applications cited in the specification are hereby incorporated in their entirety by reference.

BACKGROUND TECHNOLOGY

Capillary valves have turned out to be useful for controlling liquid transport in centrifugal-based microfluidic devices. One of the main advantages has been that neither this kind of valves nor centrifugal force requires mechanical means on-board a microfluidic device. Capillary valves are stops for a liquid flow/transport and are not to be confused with flow restrictions that permit flow but reduce the flow rates (impede flow). Once a liquid front is breaking through a capillary valve there is in principle no hinder for the ongoing flow or for restarting after a stop (as long as contact with liquid is maintained).

The use of capillary or surface tension stop functions in the form of valves, vents, anti-wicking means etc in centrifugal-based microfluidic systems has been described by Gamera Biosciences and Gyros AB, among others: WO 9853311, WO 0078455, WO 0187486, WO 0079285; WO 0187487; WO 2004058406; WO 9807019 (all of Tecan Trading/Gamera Biosciences) and WO 9958245; WO 0040750; WO 0147638; WO 0185602; WO 0274438; WO 0275312; WO 03018198; WO 03024598; WO 04103890; WO 04103891; etc (all of Gyros AB).

According to the Gamera/Tecan publications an increase in cross-sectional dimension to obtain a capillary valve in a hydrophilic microchannel could be anything from continuous to abrupt. Our work with microfluidic devices has primarily dealt with devices replicated in plastic material. It is our experience that capillary valving based on increases in cross-sectional dimensions requires extremely sharp and distinct changes of a kind not recognized in WO 9807019. Conventional embossing, injection moulding etc and other replication techniques thus seem insufficient for the manufacture of microfluidic valves based on a change in cross-sectional dimension. In order to distinguish changes that create a valving effect from other changes the former will be called "sharp" increases/changes compared to other changes that have no or only an insignificant valving effect.

Another centrifugal based approach is given by the company Abaxis. See for instance U.S. Pat. No. 5,186,844, U.S. Pat. No. 5,242,606, U.S. Pat. Nos. 5,693,233, 5,160,702 etc and J. Autom. Chem. 17(3) (1995) 99-104 (Schembri et al). In Abaxis' system the flow resistance in a channel going between the reservoirs controls the flow between an inner reservoir and an outer reservoir. Compare also U.S. Pat. No.

6,632,656 (Gyros AB). In some instances the flow between an inner and an outer reservoir is controlled by so called siphons, i.e. the channel concerned is of capillary dimensions starts from the inner reservoir by making an inward turn (elbow) before ending in the outer reservoir. At a sufficiently high spin speed centrifugal force will prevent liquid from passing over the extreme of the elbow. When the spin speed is slowed down and/or stopped wicking starts transporting liquid over the extreme. Resumed spinning further supports this liquid transport. An inner reservoir may be designed as a separation unit for separating off suspended particulate material, such as cells, from a liquid, such as blood. In order to safely retain the particulate material in the reservoir the bottom of the of the reservoir has weirs delineating the outer part from the inner part of the reservoir such that the particulate material will be maintained in the outer part even when spinning is decreased or stopped. Mixing can be accomplished in mixing chambers containing two different aliquots by cycles of forward and reversed spinning or of accelerated and decelerated spinning.

In conclusion:

Gyros' system primarily contemplates processing nl-aliquots of liquid containing reagents by the use of centrifugal force and/or capillary force in hydrophilic microconduits. Starting aliquots containing an uncharacterized entity, e.g. an analyte, may be in the μl-range, such as ≦30 μl or ≦20 μl. Earth's gravity is as a rule not of interest.

Abaxis' system utilizes considerably larger volumes and dimensions, together with centrifugal force and gravity. The wettability of the channels and capillary force is of minor interest (except for the siphons discussed above). Starting aliquots containing an uncharacterized entity and reagent aliquots are typically well above the nl-range, such as ≧10 μl or ≧30 μl or ≧30 μl. In many cases the channels are large enough to permit entrance of liquid into non-vented reservoirs without risk for inclusion of air bubbles (filling and venting in parallel through the same channel).

Tecan's system is intermediary to Gyros' and Abaxis' systems.

OBJECTS OF THE VARIOUS ASPECTS OF THE INVENTION

Unit A: Technical problems and/or advantages: There is often a need in centrifugal-based system to link two capillary valves (I and II) in series such that a liquid passing through an upper capillary valve I shall be collected at a lower capillary valve II. Collection of liquid at valve II will mean that a liquid plug height will be built up which in turn means that the risk for the liquid to leak through valve II will increase while liquid is being collected at this valve. Risks for uncontrolled flow through are also at hand for other through-flow functional units that require a controlled flow and are present downstream of an upper valve I. A typical example is a reaction microcavity containing a solid phase (e.g. porous bed) with an immobilized reactant that is to be reacted under flow conditions with a reactant dissolved in a liquid entering the microcavity from valve I.

We have managed to lower these risks by placing valve I in a microconduit I that has an inlet end at a higher level than its outlet end in combination with designing the microconduit to support formation of a liquid plug that extends continuously downstream from valve I to a liquid front that is within microconduit I and at a lower level than the inlet end. The creation of a positive plug height between the liquid front and the inlet end will support and facilitate downstream transport of liquid.

As a consequence the spin speed for transport of liquid from an upstream microcavity I having a liquid outlet I connected to the inlet end of microconduit I can be reduced with a concomitant reduction of the risk for undesired flow through of a valve (=valve II) or a downstream porous bed.

We have also recognized that additional positive effects can be achieved if unit A is linked to or comprises one or more characteristic features of at least one of the functional units B-F.

Unit B: Technical problems and/or advantages: It would be beneficial to have a simple method for the manufacture of a capillary valve for which the spin speed/centrifugal force for break-through of liquid flow easily could be varied in a predetermined manner during the manufacture. The solution to this problem is to place the capillary valve in an upwardly directed segment of a microconduit that in the upstream direction is in liquid communication with a microcavity containing a liquid, the upper level of which is above or at about the same level as the uppermost level of the microconduit. The centrifugal force/spin speed required for liquid to break through the valve will depend on the level of the valve relative to the spin axis. A valve placed at a higher level in the upwardly directed segment will require a higher spin speed compared to a valve placed at a lower level.

We have also realized that further advantages can be accomplished if unit B also is linked to or comprises one or more characteristic features of at least one of the functional units A and C-F.

Unit C: Technical problems and/or advantages: We have recognized that creation of a liquid plug in a downwardly directed hydrophilic microconduit after liquid has passed a capillary valve in the microconduit is associated with problems. Air bubbles will easily be included, surface transport (wicking) may be quicker than plug transport, etc. We have accomplished to minimize these problems by locally dividing the microconduit at the valve position in two or more microchannels (=fingers) with the aim to increase the available amount of liquid per time unit for plug formation. At both sides of the stop function/valve function, the microchannels start from or exit into a space that is common for all of them. At least two of the microchannels are functionally equal in the sense that the liquid front breaks through them in parallel as defined elsewhere in this specification. Further improvements may be accomplished if it is secured that the sum of the cross-sectional areas of the microchannels are lower than the cross-sectional area of the microconduit downstream of the microchannels. We have also realized that similar designs also are favourable as vent functions to level out overpressure/subpressure created in microfluidic devices during their use.

We have also realized that further improvements can be accomplished if this unit linked to or comprises one or more characteristic features of at least one of the functional units A-B and D-F.

Unit D: Technical problems and/or advantages: The efficiency of a capillary valve may have a tendency to go down when contacted with liquids that contains materials that can negatively affect this kind of valves, e.g. surface active materials and materials that can precipitate in and/or clog microchannels. Finger valves as defined for unit C may be particular prone to clogging. Therefore it may be advantageous to protect capillary valves from unnecessary contact with this kind of liquids.

We have accomplished this kind of protection by introducing an additional capillary valve function in the same microconduit as the capillary valve to be protected. The additional valve is upstream of the valve to be protected.

We have also realized that further improvements can be accomplished if unit D is linked to or comprises one or more characteristic features of at least one of the functional units A-C and E-F.

Unit E: Technical problems and/or advantages: This unit comprises a separation microcavity I in which a liquid containing denser material and lighter material is separated by centrifugation to obtain a phase system comprising a lower phase and an upper phase. The denser material will partition to the lower phase. It may be particles like cells and solid phases in the form of particles and other particulate materials that are suspensible in the liquid phase and have a larger density than the liquid phase. The lighter material will partition to the upper phase and is typically a liquid phase containing dissolved material, i.e. particle-depleted liquid such as plasma, supernatants from cell culture, cell homogenates, tissue homogenats and from other biologically derived fluids containing particulate material. See for instance WO 2002074438 (Gyros AB), WO 9853311 (Tecan Trading/Gamera Biosciences), US 20040121449 (Bayer Healthcare), U.S. Pat. No. 5,186,844, U.S. Pat. No. 5,242,606, U.S. Pat. No. 5,693,233 etc (Abaxis), and J. Autom. Chem. 17(3) (1995) 99-104 (Schembri et al). After centrifugation, the upper phase is transferred via a liquid outlet I on the separation microcavity and an outlet microconduit I to a separate microcavity II in which further processing is taking place. WO 2002074438 (Gyros AB) suggests that microconduit I shall be directed slightly outwards at its connection to the separation microcavity with a capillary valve in the form of a hydrophobic break directly associated with the connection. WO 9853311 (Gamera Biosciences) suggests two variants for selectively transporting an upper plasma phase to a separate microcavity II: a) a closing valve (wax valve, FIG. 9), or a variant in which the upper plasma level is adjustable upwards after formation of the phase system (FIG. 10). US 20040121449 (Bayer Healthcare) suggests a downwardly directed outlet microconduit containing a hydrophilic or a hydrophobic stop. Abaxis with their larger volumes suggests that the outlet microconduit I for the upper phase may be directed among others tangentially or inwards/upwards (U.S. Pat. No. 5,186,844, U.S. Pat. No. 5,242,606, U.S. Pat. No. 5,693,233 etc, and J. Autom. Chem. 17(3) (1995) 99-104 (Schembri et al)).

We have recognized that improvements are required for microfluidic separation units in order to
a) prepare particle-depleted fractions of sufficiently high quality,
b) integrate preparation of particle-depleted liquids with accurate metering and/or further processing in microfluidic devices, and/or Lowering of the amount of particles in liquids initially containing suspended particles typically requires high g-forces/spin speeds and high risks for malfunctioning of valves and other through-flow functional units that might be present downstream a separation unit in a microfluidic device. Malfunctioning includes among others precipitation and/or clogging of finger valves, porous beds, narrow microconduits etc. See the discussion above for unit A.

We have realized that improvements can be accomplished in the case microconduit I connected to liquid outlet I comprises an upward segment next to liquid outlet I, preferably with a capillary valve I being associated with this segment. This means that liquid outlet I with preference should be placed in an upwardly directed part of the inner wall of microcavity I. In other words the transport direction through liquid outlet I should be upwards. According to our innovative concept advantages may also be achieved for other transport directions through liquid outlet I. The capillary valve may be directly associated with liquid outlet I and is preferably a finger valve.

We have also realized that further improvements can be accomplished if unit D is linked to or comprises one or more characteristic features of at least one of the functional units A-C and E-F.

Unit F: Technical problems and/or advantages: Microfluidic detection microcavities in which a result of a reaction taking place in an upstream reaction microcavity is read in a solution have typically been in the form of a microconduit or a chamber. In many cases the detection microcavity contains a liquid that is displaced by the solution coming from the reaction microcavity and containing molecular entities reflecting the result. In conventional types of microfluidic detection microcavities this kind of design typically means a significant risk for the incoming solution to mix with the liquid that preoccupies the detection microcavity. This adverse effect has in particular been found disturbing in centrifugal based systems. Mixing at this stage is not desirable because it will lower the concentrations of the entities to be detected/measured.

We have now recognized a way to lower this kind of undesired mixing which is suitable for centrifugal-based microfluidic devices. Our proposal is to design the detection microcavity as a microconduit that has an inlet part, an outlet part, and between these two parts defines one or more vertical meanders each of which comprises at least two returns. The section between two returns is called an intermediary section and a return between the first and the last return is called an intermediary return. The meander may be directed upwards with the main flow direction being upwards, i.e. the inlet part is at a lower level than the outlet part (upward meander). The meander may alternatively be directed downwards with the main flow direction being downwards, i.e. the inlet part is at a higher level than the outlet part (downward meander).

Microconduits comprising lying meanders and used as distribution manifolds have been described in WO 02074438, WO 02075312, WO 03093802; WO 03018198; WO 03024598; WO 0450247; WO 04083108; WO 04083109; and WO 04106926 (all of Gyros AB). Microconduits comprising standing meanders and used as mixing microconduits have been described in WO 00078455; WO 00079285; and WO 01087487 (all of Gamera Biosciences/Tecan Trading). According to WO 01087487, measurements and/or performing reactions can also be carried out in a meandering mixing microconduit.

THE INVENTION

The present invention is a microfluidic device of the type generally described under the headings Technical Field and General about Microfluidic Devices. The characteristic feature of the device is that at least one, two or more of the microchannel structures of the device comprise at least one of the functional units A-F with the features as described in this specification.

For each unit there is also a corresponding innovative method comprising the use of the device and/or a microchannel structure and/or a functional unit of the present invention for transporting and/or processing one or more aliquots of liquid. At least one of the aliquots contains a reactant of a preparative, synthetic or analytical process protocol. This reactant may be an uncharacterized entity (analyte) or a reagent contained in a sample (aliquot) to be processed. The protocols are typical within the field of chemistry, biology, medicine etc A microconduit, such as microconduit I or II in the various inventive units, is a part of a microchannel structure and comprises one inlet end and one outlet end. If not otherwise specified a microconduit is intended for transport of one or more aliquots of liquid that may or may not contain one or more of the above-mentioned reactants. Between the inlet end and the outlet end of a liquid transport microconduit there may be a capillary stop function in the form of a capillary valve or capillary vent, but no distinct microcavities (unless they are used solely for defining a capillary valve or vent) and no branchings involving other liquid transport microconduits. One or more vent microconduits may be connected to a liquid transport microconduit. If not otherwise specified a vent microconduit is solely used for transport of air/gas in order to level out overpressure or subpressure that might be created within the microchannel structure during the transport and/or processing of liquids. Between the ends of a vent microconduit there may be a microcavity.

An inlet end of a microconduit that is directly connected to a liquid outlet of a microcavity includes that the end and the outlet are coinciding. Thus a valve or a vent that is placed in or at a microconduit inlet end that is directly connected to a liquid outlet of a microcavity is also placed in or at the liquid outlet. Similarly also applies for the outlet end of a microconduit that is directly attached to the liquid inlet of a microcavity.

The position of a stop capillary valve shall be considered to be the position at which the front meniscus stops.

Non-closing valves such as capillary valves also comprise a vent function.

A. Unit Supporting Downstream Transport from a Capillary Valve by Creation of a Driving Liquid Plug This functional unit comprises:
a) an upstream microcavity I (4) with a liquid inlet I (5) and a liquid outlet I (6),
b) a microconduit I (17) that has an inlet end (16) and an outlet end (18), and
c) a capillary valve I (24) that is associated with microconduit I (17).

The upstream microcavity (4) is intended for retaining a liquid aliquot which defines an upper liquid level I in the microcavity. This upper liquid level is equal to or lower than the level of the uppermost part of the microcavity (4) (typically at the level of liquid inlet I (5)) and also above the level of liquid outlet I (6).

The device (1) and the microchannel structure (2) containing the unit as well as the unit itself are designed to permit spinning about a spin axis (3) in order to drive liquid placed in the upstream microcavity (4) to exit the microcavity via liquid outlet I (6) and further downstream via microconduit I (17). The transport primarily is caused by centrifugal force created by the spinning and/or by hydrostatic pressure built up in the individual microchannel structures during spinning and/or by capillary force. Capillary force sufficient to cause self-suction may be used as a supplement when the spinning and/or hydrostatic pressure are/is insufficient for the transport, for instance during non- or low-spinning conditions and in particular when a liquid aliquot or at least its front meniscus shall be brought to a position closer to the spin axis (3) and/or from a liquid inlet port (9,51,52,53) to the first valve or vent (15a, 15b,24 or 25 for 9; 54,57 for 51; 55 for 52; 56,58 for 53) of a microchannel structure (1) (port (9,51,52,53)=opening in the surface of the device).

The main characteristic feature is that
i) liquid outlet I (6), i.e. also the inlet end (16) of microconduit I (17), is closer to the spin axis (3) than the outlet end (18) of microconduit I, and
ii) capillary valve I (24) is placed a) at liquid outlet I (6), or b) between the inlet and the outlet ends (16 and 18, respectively) of microconduit I (17), and
iii) the difference in radial distance between liquid outlet (6) of the upstream microcavity (4) or valve I (24) and the outlet end (18) of microconduit I (17) is typically 5%, such as 10% or 50% or 100% or 200% or 500%, of the difference in radial distance between the uppermost part (7) of the upstream microcavity (4) and liquid outlet I (6) or valve I (24), such as of the difference in radial distance between upper liquid level I and liquid outlet I (6) or valve I (24).

The upper liquid level I is always equal or lower than the level of the uppermost part (7) of the microcavity (4).

The part of microconduit I (17) that is downstream of valve I (24) is designed to be capable of supporting liquid transport as a continuous liquid plug extending from the inlet end (16) of microconduit I (17) (and also from valve I (24)) to a liquid front (front meniscus) that is within the microconduit (17) and also below the level of the inlet end (16) of the microconduit (17). The upper liquid level I at the start of the transport then corresponds to the rear meniscus which initially is moving downwards in the upstream microcavity (4) and then upwards/downwards in microconduit I (17) depending on it's the shape of the microconduit. The maximal height of this plug is equal to the difference in radial positions of the inlet end (16) and the outlet end (18) of microconduit I (17), but in practice will depend on a number of factors such as cross-dimensions of the microconduit, kind of liquid, flow rate etc. Once the meniscus has passed valve I (24) and an upper extreme (22) (if present), the plug will grow downwardly permitting a lowering of the spin speed. The requirements for obtaining this kind of plug transport depends on a number of factors such as: dimension, position and shape of the upstream microcavity, microconduit I, and the liquid outlet of the microcavity; surface tension of the liquid; applied centrifugal force, kind of capillary valve including dimensions; wettability of inner surfaces in the upstream microcavity and in microconduit I; etc. Optimal combinations of numerical values of various features are represented in the drawings and in other parts of this specification. A widening of the microconduit and/or at its outlet end (18) counteracts liquid plug extension. Experimental testing is required in each particular case. See the experimental part.

Liquid inlet I (5) is typically in the top (7) of the upstream microcavity (4) and directly connected to an inlet microconduit (8a) that in the upstream direction communicates with a liquid inlet port (5), i.e. with an opening in the surface of the device for introduction of liquid. The inlet microconduit (8a) preferably has an overflow opening (10) at the same level as liquid inlet I (5). The overflow opening (10), if present, defines the top or uppermost part (7) of the upstream microcavity (4). See further below.

Liquid inlet I (5) is typically at a position above the level of liquid outlet I (6). If not, then the unit contains appropriate valving for preventing back-flow through liquid inlet I after the upstream microcavity has been filled to a desired level (=upper liquid level I).

The upstream microcavity has an inherent vent function in liquid outlet I (6) in the case valve I (24) is a non-closing valve such as a passive valve. There may also be one or more additional vent functions in the upstream microcavity for hindering undesired air bubble formation within the microcavity (not shown in drawings). These other vent functions may be associated with a pure gas vent or an additional inlet for liquid. See below.

The liquid flow starting to exit through liquid outlet I (6) may have various directions in relation to the centrifugal force at the liquid outlet I (6). The flow direction may thus comprise (a) a downward/outward component (outward radial component), or (b) an upward/inward component (inward radial component), or (c) essentially tangential (horizontal). The flow direction relative to the direction of the centrifugal force at liquid outlet I (6) may thus be for alternative (a) at least partially in the same direction (along) as the centrifugal force, for alternative (b) at least partially against the centrifugal force, and for alternative (c) essentially orthogonal to the centrifugal force. Expressed as an angle ($\alpha$) relative to the direction of centrifugal force at liquid outlet I this may be for alternative (a) $0° \leq \alpha \leq 90°$ such as $0° \leq \alpha \leq 85°$ (along), for alternative (b) $90° \leq \alpha \leq 180°$, such as $95° \leq \alpha \leq 180°$ (against), and for alternative (c) $80° \leq \alpha \leq 100°$, such as $85° \leq \alpha \leq 95°$, and in particular 90° (orthogonal).

The angle ($\alpha'$) between the centrifugal force at liquid outlet I and the inner wall around liquid outlet I and/or the opening as such may be for alternative (a) $0° \leq \alpha' < 90°$, such as $10° \leq \alpha' \leq 90°$, for alternative (b) $0 \leq \alpha' \leq 90°$, such as $10° \leq \alpha' \leq 90°$ and for alternative (c) $0° \leq \alpha' \leq 10°$, such as $0° \leq \alpha' \leq 5°$ or in particular $\alpha' = 0°$. These intervals refer to the angle seen from the interior of the microcavity and regarded downward/upward.

The part of microconduit I (17) that is next to liquid outlet I (6) of the upstream microcavity (4) preferably has a direction selected amongst the main directions for flow through this liquid outlet (6) although the two directions do not need to be the same Microconduit I (17) may be directed continuously downwards, for instance a) be straight and coincide with or angled relative to a straight line (radius) going from the spin axis to liquid outlet I/inlet end (6/16) of microconduit I (17), or b) contain a curvature, such as in a meander or in single curved variants like in evolvents. Alternatively microconduit I (17) may contain one or more upwardly and one or more downwardly directed sections (23*a* and *b*, respectively) between which there may be upward or downward turns ("elbows") and/or horizontal sections.

In certain variants, microconduit I (17) comprises one upward turn that has an upper extreme ("elbow") (22) that is at an intermediary level between the level of liquid outlet I (6) and the uppermost part (7) of the upstream microcavity (4), typically between the level of liquid outlet I (6) and upper liquid level I. In other preferred variants, the level of the upper extreme (22) may be above or equal to upper liquid level I, e.g. above or equal to the level of the uppermost part (7) of the upstream microcavity (4). All parts of microconduit I (17) between the inlet end (16) and the upper extreme (22) in the variants of this paragraph are preferably above the level of liquid outlet I (6), typically as a microconduit section (23*a*) that is continuously directed upwards. Similarly the parts (23*b*) of microconduit I (17) that are between the upper extreme (22) and the outlet end (18) are preferably directed continuously downwards.

Downwardly directed sections, upwardly directed sections, horizontal sections, upward turns, downward turns etc may be as described for units B and C and/or for the corresponding use aspects.

Capillary valve I (22) is typically positioned a) at the inlet end (16) of microconduit I (17) (coincides with liquid outlet I (6)), or b) between the inlet and the outlet ends (16,18) of microconduit I (17), or c) at the outlet end (18) of microconduit I (17).

Valve I (24) may be located either before or after an upper extreme (22). If microconduit I (17) is a single downward section, valve I (24) is at the level of the inlet end (16) of microconduit I (17) (=level of liquid outlet I (6)) or below this level. If microconduit I (17) is an upward turn with an upper extreme (22), valve I (24) is preferably placed in the upward section (23*a*) of the turn at a height as discussed for unit E. Valve I (24) may also be placed in the downward section (23*b*). In the case the upper extreme (22) is above the level of upper liquid level I or above the level of the uppermost part (7) of the upstream microcavity (4), valve I (24) is preferably placed below the relevant ones of these levels or alternatively sufficient hydrostatic pressure is created by adding extra liquid on the rear meniscus in the upstream microcavity (4) when the unit is in use. Valve I (24) is typically placed at a level relative to liquid outlet I (6) that is above 25% of the height between the inlet end (16) (=liquid outlet I (6) and the upper extreme (22), e.g. as part of an upward section (23*a*) of an upward turn (elbow) of microconduit I (17). The preferred relative position of the valve within this interval is preferably even higher, such as above 50% or above 75% of the height between inlet end (16) and the upper extreme (22). See also units B, C and E and the use aspect of unit A-C and E in which also other relative positions are given.

Capillary valves in the unit, such as valve I (24), are typically based on a change in chemical and/or geometric inner surface characteristics according to principles that are well-known in the field. The change may be as a sharp increase or decrease in a cross-sectional dimension of a microconduit (lateral change) and/or a sharp increase in non-wettability of an inner surface of a hydrophilic microconduit, in both cases in the flow direction. The change is typical local (break), for instance a non-wettable/hydrophobic surface break in an otherwise hydrophilic flow path. See "General about Microfluidic Devices" and Background Technology and publications referenced therein. Valve I (24) is preferably a finger valve as defined in this specification in the context of units C and E.

Microconduit I (17) may contain an additional capillary valve (25) upstream of valve I (24) provided valve I is placed in the microconduit and in particular if valve I is a finger valve. See further unit D. For variants where the upstream microcavity is a separation microcavity as described for unit E this kind of extra valve (25) may reduce the risk for contamination and/or clogging of valve I (24) by material that is to be separated from the liquid phase intended to pass through microconduit I. See units D and E.

The cross-sectional area in the upstream microcavity (4) is preferably larger upstream of liquid outlet I (6) than in microconduit I (17), e.g. with a factor $\geq 1$, such as $\geq 2$ or $\geq 5$ or $\geq 10$. The cross-sectional area of microconduit I upstream of valve I is preferably larger than downstream of the valve with a factor e.g. $\geq 1$, such as $\geq 2$ or $\geq 5$ or $\geq 10$. These latter intervals in particular apply if valve I is a capillary stop function in the form of a finger valve, such as described in unit C.

Liquid outlet I (6) may divide the upstream microcavity (4) in a lower part (4*b*) and an upper part (4*a*) as discussed for unit E below, in particular if the microcavity (4) is to be used for the separation of denser material from lighter material that are present in a liquid. In typical cases the lower part (4*b*) then constitutes $\geq 10\%$, such as $\geq 25\%$ or $\geq 50\%$ or $\geq 70\%$ or $\geq 80\%$ of the total volume of the upstream microcavity (4). The exact relative volumes of the parts is determined by the relative volume of the phase to be exported through liquid outlet. See unit E.

The upstream microcavity is typically tapered towards the level of liquid outlet I (6) (or towards the outlet (6) as such), thus having a smaller cross-sectional area at this level compared to the largest cross-sectional area upstream of liquid outlet I (6). In the case the upstream microcavity (4) is divided into an upper and lower part (4*a*,4*b*), there is typically a constriction of the microcavity (4) defining the upper part (4a) and the lower part (4b). The constriction is then essentially at the same level as liquid outlet I (6) and typically defined by tapering the upper and/or lower part towards this level. The tapering/constriction in this variant means that the cross-sectional area at liquid outlet I (6) is smaller than the largest cross-sectional area of one or both of the parts, preferably of the upper part (4a). Tapering may also be towards liquid inlet I (5). Se further below and the description of unit E.

The lower part (4b) (if present) is typically communicating with one or more outlets (14) to ambient atmosphere solely for venting out air displaced by liquid entering this part (4b). The opening (port) (14) in the surface of the device for an outlet of this kind is preferably located at a higher level than the level of a liquid inlet (5) of the upstream microcavity (4) and typically also at a higher level than the level of corresponding inlet port (9) for the same microcavity. There may be a capillary stop function (downstream end) (15a) associated with this kind of outlet(s) (14), in particular if the corresponding opening in the surface of the device is at a lower position than the level of liquid inlet of the upstream microcavity. The upper part (4a) of the upstream microcavity (4) may be used as a volume-metering microcavity. See below. This metering is likely to be more accurate if the capillary stop function (15a) associated with a vent function of the lower part (4b) is placed at a lower level than liquid outlet I (6). See also unit D for further details.

The lower part (4b) (if present) may also have a separate liquid outlet I' (not shown) for export of material from the lower part after the upper part has been emptied via liquid outlet I. In this case liquid outlet I' is at a lower level than liquid outlet I.

A capillary stop function (15a) associated an outlet for the lower part (4b) is preferably non-closing, e.g. in the form of a capillary valve or a capillary vent (preferably a finger vent as described for unit C). Compare WO 02074438 (Gyros AB), for instance unit 12 therein.

The total volume of the upstream microcavity (4) is the maximal liquid volume that can be retained between the level of the uppermost part (7) (typically liquid inlet I (5)) and the level of the lowest part, typically the level of liquid outlet I (6).

Functional unit A may also comprise a downstream microcavity II (20) with a liquid inlet II (21) that is in fluid communication with the outlet end (16) of microconduit I (17). This microcavity (20) typically also has one or more outlets, for instance
 a) a liquid outlet arrangement II which comprises a liquid outlet II (32) of microcavity II (20) and an outlet microconduit II (35) and in which transport of material out of the microcavity is controlled, and/or
 b) one or more vent functions.

The transport controlling function of arrangement II is typically achieved by placing a constriction (33) at liquid outlet II (32) that prevents particulate material, such as the particles of packed porous bed, from escaping microcavity II (20) and/or by including liquid flow restrictions in the arrangement and/or a valve II, typically a capillary valve. Valve II is typically placed in microconduit II (35), typically at liquid outlet II (32). Flow restrictions in the form of a porous bed (34) may be placed in the microcavity, preferably at its outlet end (WO 02075312 Gyros AB). Flow restrictions may also be inherent in the design of microconduit II (35), i.e. the microconduit is long and/or narrow (WO 03024598 Gyros AB) and/or by including other characteristics that support impeded flow, such as rough inner surfaces, porous plugs, pillars, etc. The downstream microcavity (20) may also have one or more additional liquid inlets (51,52,53) that may or may not coincide with one or more of the vent functions. Each of one, two or more of these extra inlets may or may not be part of an inlet arrangement that is individual for one single microchannel structure or common for several microchannel structures and providing a volume-defining unit with a volume-metering microcavity per microchannel structure as described in General about Microfluidic Devices further below.

Liquid outlet II (32) is typically placed at the lowest part of the downstream microcavity (20) but may also be located at an intermediary level between the levels of lowest and the uppermost part thereby dividing the downstream microcavity in an upper part and a lower part. In the latter variant the lower part may comprise a separate liquid outlet II' comprising a valve II'. The design of the liquid inlets, liquid outlets, valves, upper and lower parts etc of the downstream microcavity may be as discussed above for the upstream microcavity.

Liquid inlet II (21) is typically closer to the spin axis (3) than any of liquid outlets II (32) and II' (if present).

Liquid outlet II (32) may be in downstream liquid communication with a detection unit, for instance as defined for unit F below. Between this liquid outlet there may be a microconduit II (35) as defined above.

Valve II and possibly also valve II', if present, are preferably passive, as discussed above and in General about Microfluidic devices, Background Technology and in publications referenced in these parts. Other types of non-closing valves may also be used. One or more of the valves that are associated with liquid outlets on the downstream microcavity (20) may be finger valves as described for unit C.

Flow restrictions in the form of a porous bed (34) are typically associated with the lowest of the liquid outlets (32) of the downstream microcavity (20). This kind of bed is typically used as a solid phase that will interact with reactants or contaminants that are present in a liquid aliquot passing through the bed. The bed is typically in the form of a porous monolithic plug or as a packed bed of porous or non-porous particles. The interaction with reactants and contaminants is typically via a reactant that is immobilized to the solid phase material of the bed. Other kinds of flow restrictions are typically used to give a controlled flow rate through the microcavity (20) including also through a porous bed placed therein. This will enable controlled residence times under flow conditions for liquid aliquots passing through the microcavity and thus also for controlled contact times between reactants immobilized in the microcavity (to walls, porous beds etc) and through-passing reactants (WO 02075312 (Gyros AB) and WO 03024598 (Gyros AB)). The term "controlled residence time" includes that the residence time is essentially equal for the corresponding microcavity in two or more microchannel structures (same device) that are used simultaneously in the same meaning as discussed in WO 02075312 and WO 03024598.

The difference in radial distance between the inlet end (16) and the outlet end (18) of microconduit I (17) is preferably $\geq 100\%$, such as $\geq 200\%$ or $\geq 500\%$ or $\geq 1000\%$, of
 a) the difference in radial distance between liquid inlet II (21) and the lowest liquid outlet (32) or capillary valve or flow restriction that is associated with the downstream microcavity (20), or
 b) the difference in radial distance between the upper liquid level in the downstream microcavity and the lowest liquid outlet valve (32) or capillary valve or flow restriction that is associated with the downstream microcavity (20).

This does not exclude that the difference in radial distance between the inlet end (16) and the outlet end (18) of microconduit I (17) may be less than the difference defined in (a) or (b) for instance ≧10%, such as ≧25% or ≧50% or ≧75%. The term "upper liquid level" (=upper liquid level II) in (b) refers to the liquid level in the downstream microcavity (20) after a desired volume of liquid has been transported from the upstream microcavity (4) to the downstream microcavity (20).

The volume of the downstream microcavity (20) beneath its half height may be ≧50%, such as ≧60% or ≧75%, of the total volume of the microcavity.

In the same manner as upstream microcavity (4) the downstream microcavity (20) may be constricted and/or tapered.

Tapering for both microcavities (4,20) typically means that at least one, two or more of the inner walls at the outlet/inlet concerned form an acute angle (β<90°) with the (main) transport direction through the tapering. This angle (β) preferably is in the interval of 10°-50°, such as 20°-40° or 25°-35° with preference for about 30°. These intervals are applicable also to pure vent outlets. With respect to liquid outlets and pure vent outlets tapering will counteract air bubble formation during filling of the microcavity with liquid.

If a microcavity (4,20) has a constriction and/or tapering associated with an inlet/outlet (5/6,32), the largest cross-sectional area of the microcavity or an upper part (4a) and/or lower part (4b) thereof is typically larger than the cross-sectional area at the level of outlet/inlet concerned with a factor >1, such as ≧1.25 or ≧1.5 or ≧3.0 or ≧5.0.

The upper part (if present) of the upstream microcavity (4) and/or of the downstream microcavity (20) may be part of a volume-defining unit, for instance of the type outlined in WO 02074438 and WO 03018198 (both of Gyros AB).

For an upstream microcavity (4) the preceding paragraph typically means that the inlet microconduit (8a) has an overflow opening (10) at the same level as the level of liquid inlet I (5). This overflow opening (10) is typically connected to a downwardly directed overflow (11) microconduit that may end above or below the levels of valves (15a, 15b,24,25) that may be associated with liquid outlet(s) (6,14) of the upstream microcavity (4). The uppermost portion of the upstream microcavity (4) is preferably constricted at and/or tapered towards the level of the overflow opening (10), i.e. also at and/or towards the level of liquid inlet I (5). See also WO 02074438 and WO 02018198 (both of Gyros AB).

The downstream microcavity (20) may also comprise a volume-defining function (not shown). This typically means that the microcavity has:
  a) a first liquid outlet that is an overflow opening and divides the microcavity in an upper part and a lower part with a first outlet microconduit that is designed as an overflow microconduit that is directly connected to the overflow opening and directed downwardly with its outlet end and a first valve that may be above or below the levels of liquid outlets and/or valves of the lower part of the microcavity, and
  b) a second liquid outlet that is i) present in the lower part of the microcavity, ii) connected to the inlet end of a second outlet microconduit that is in downstream liquid communication with downstream parts of the microchannel structure, and iii) associated with a second valve that is present at the second liquid outlet and/or in the second microconduit.

In this design the lower part of the microcavity corresponds to a volume-metering microcavity, the first liquid outlet corresponds to liquid outlet II (32) in the drawings and the second liquid outlet is not shown in the variant of the drawing. Valves, such as the first and second valves are typically non-closing valves, such as capillary valves with the preference for designs as contemplated elsewhere in this specification.

Constrictions and taperings are as outlined for the corresponding positions in the upstream microcavity. See above and also unit E.

The microchannel structure in the innovative device may comprise at least two units of A serially linked to each other such that the downstream microcavity of an upstream unit is in liquid communication with the upstream microcavity of the closest downstream unit. The serially linked units may be different in the sense that identical operations are not to be carried out in the upstream or downstream microcavity of an upstream unit as in corresponding microcavities in a downstream unit. The downstream microcavity of an upstream unit may coincide with the upstream microcavity of the closest downstream unit. If the upstream and downstream microcavities of two consecutive units do not coincide other functional units may have been inserted between them.

An upstream microcavity (4) may comprise a) a mixing and/or diluting function in which case there typically are two or more liquid inlets on the microcavity, b) a function for separating a less dense material from a denser material as discussed for unit E below, c) a function for carrying out one or more biochemical reactions typically selected amongst reactions involving cells or parts of cells, enzyme reactions, affinity reactions etc, and other chemical reactions (including also biochemical reactions), etc. The function of the upstream microcavity (4) may be selected amongst the same general functions as for the downstream microcavity (20) (see above) and vice versa for the downstream microcavity (20). The functions of the two microcavities will typically differ with respect to what is actually carried out in each of them. The upstream microcavity (4) may be equipped with one, two, three or more inlets that are part of inlet arrangements as described above for the downstream microcavity (20).

In the case a microcavity is designed for carrying out reactions of the types given these reactions are typically between dissolved reactants and/or between one or more dissolved reactants and a reactant/reactants firmly associated with a solid phase retained in the microcavity concerned. If an upstream microcavity comprises a separation or fractionation function as described above and for unit E, the reaction microcavity is typically a downstream microcavity. In this context the term "dissolved reactant" includes a suspended reactant, e.g. a cell or a part of a cell, a reactant immobilised to a particulate solid phase that is in suspended form in the microcavity etc. The term "retained" means that the solid phase is maintained in the microcavity during the reaction and also after liquid that may be present during the reaction has been at least partially removed. Typically such solid phases are inner walls, porous beds, for instance porous monoliths and packed beds of particles preferably placed in the downstream end of the microcavity and/or in an outlet microconduit, e.g. microconduit I, or II or II'. In the case a porous bed is associated with an outlet, there is typically no separate valve function associated with the outlet. The possibility for performing reactions in a microcavity is typically combined with performing mixing and/or diluting in a pre-step in the same microcavity or in an upstream microcavity (if present).

One inventive aspect related to unit A is a method utilizing a microfluidic device in which there is a microchannel structure comprising the innovative unit A. This method comprises the steps of:
  i) providing a microfluidic device (1) in which there is a microchannel structure (2) comprising unit A as defined above, the upstream microcavity of said unit being filled with liquid up to upper liquid level I, i.e. with a rear meniscus at the upper liquid level and a front meniscus at valve I (24) in microconduit I (17);

ii) moving the front meniscus by spinning the device (1) about the spin axis (3) at a spin speed such that the front meniscus passes valve I (24); and iii) emptying the microcavity (4) down to liquid outlet I (5) by adjusting the spin speed such that a liquid plug continuously extends within microconduit I (17) from valve I (24) with the front meniscus moving downstream to the outlet end (18) of microconduit I (17) thereby discharging liquid from the upstream microcavity (4) through the outlet end of microconduit I (17) so that the rear meniscus passes into and if possibly through microconduit I (17).

If the microcavity (4) has a lower part (4b), a new meniscus will be created inside the microcavity at the level of liquid outlet (6). In the case microconduit I comprises an upper extreme (22) that is above upper liquid level I and valve I (24) is positioned upstream the upper extreme (i.e. below upper liquid level I) the sequence "(ii) and (iii)" comprises the steps:

(ii.a) moving the front meniscus over valve I (24) by spinning the device such that the front meniscus passes the valve, (ii.b) equilibrating the liquid with or without spinning such that the front and rear meniscuses will be at equal level;

(ii.c) adjusting the spin speed, possibly by halting spinning if necessary, such that capillary force will be larger than centrifugal force at the front meniscus thereby permitting capillary liquid transport over the upper extreme (22) until the front meniscus is below the level of the rear meniscus; and (iii') emptying the upstream microcavity (4) down to the level of liquid outlet I (6) via the outlet end (18) of microconduit I (17).

During step (ii.b) the spin speed can be heavily increased, in principle only limited by the material properties of the microfluidic device. Accordingly very efficient centrifugal-based fractionation of denser material from lighter materials to upper and lower phases can be accomplished within the upstream microcavity. Steps (iii) and (iii') may alternatively also comprise liquid transport without imperative requirement for the formation of a continuous liquid plug from valve I.

When the driving plug height (between the front and rear meniscuses) is growing the spin speed/centrifugal force can be successive lowered or lowered in one or more steps. This will lower the risk for undesired and/or uncontrolled transport of liquid through liquid outlet II (32) of the downstream microcavity (20). This risk is caused by the increase in liquid height/hydrostatic pressure caused by the liquid transported to the downstream microcavity (20). In the ideal case spin speed and the design of unit A should be adapted to each other such that the liquid height in the downstream microcavity during at least a part of the last half part of the transport is less than the sum of the driving liquid heights in the upstream microcavity (4) and microconduit I (18), for instance with a factor $F \leq 1$, such as $\leq 0.75$ or $\leq 0.5$ or $\leq 0.25$ or $\leq 0.1$. In the ideal case it may be favourable if this condition is full-filled during the whole time for the transport. This way of performing steps (iii) and/or (iii') may be supported if a) the height of the upstream microcavity (4) is larger than the height of the downstream microcavity (20), for instance larger with a factor $F' \geq 1$, such as $\geq 1.5$ or $\geq 3$ or $\geq 5$ or $\geq 10$, and/or b) the largest cross-sectional area of the downstream microcavity (20), for instance below 60% of its height, is larger than the largest cross-sectional area of the upstream microcavity (4), and/or c) the volume of the downstream microcavity is larger (20) than the volume of the upstream microcavity (4), e.g. with a factor $F'' \geq 1$, such as $\geq 1.5$ or $\geq 2 \geq 5$.

The height of the upstream microcavity (4) is then considered to be between the level of the top (7) and the level of the lowest liquid outlet comprising a capillary valve, e.g. liquid outlet I (6). The height of the downstream microcavity (20) is then considered to be between the level of liquid inlet II (21) and the lowest liquid outlet comprising a capillary valve, e.g. liquid outlet II (32). This does not exclude that the height of the upstream microcavity may be less than the height of the downstream microcavity, e.g. F' is <1, such as $\leq 0.75$ or $\leq 0.50$ or $\leq 0.25$. This part of the inventive aspects of unit A is also supported if there is an upper extreme in microconduit I as discussed elsewhere above and in the context of units B, C and E.

The actual spin speeds (spin program) required for the different steps depend in a complex manner on a large number of factors and is typically determined before an actual process protocol is to be carried out. For steps (iii) (and iii') it is often advantageous to successively reduce the spin speed, for instance by starting the step with a relatively high spin speed and then reducing the spin speed with a factor $\geq 0.10$, such as $\geq 0.20$ or more in one step, followed by a smoother reduction in several steps or continuously. Successive reduction of spin speed is particular advantageous in the case the unit comprises a downstream microcavity (20) to which capillary valves as described above are/is associated.

The upstream microcavity (4) or an upper part (4b) thereof may be a volume-metering microcavity of a volume-defining unit having an overflow microconduit (11) linked to the upstream microcavity at the level of liquid inlet I (5). In this case step (i) typically comprises a) providing an excess of liquid in the upstream microcavity (4) such that the microcavity (4a-4b) is filled and the excess is placed in the overflow microconduit (11) down to an overflow valve (15b) therein and in the inlet microconduit (8a), and b) spinning the device about the spin axis at a spin speed that forces the liquid in the overflow microconduit (11) and in the inlet microconduit (8a) out through the overflow valve (15b) while the liquid in the upstream microcavity remains therein.

This spin speed is lower than the spin speed required for driving liquid out through valve I (24) (and valve I' (25), if present), since the valve (15b) in the overflow microconduit (11) is designed to be weaker than other liquid outlet valves (24 and 25 (if present) associated with the upstream microcavity (4). See for instance WO 02075312, WO 02075775, WO 04083108 (all of Gyros AB) etc. This will also mean that the rear meniscus in after step (ii.b) may be below the liquid inlet/overflow opening (5,10) of the upstream microcavity (4).

Variants of unit A in which liquid outlet I (5) divides the upstream microcavity (4) into an upper part (4a) and a lower part (4b) as discussed above can be used for separation of a liquid that contains denser material and less dense material (lighter material) into an upper phase that contains the lighter material and is placed and a lower phase that contains the denser material by spinning the device containing the unit about a spin axis. The actual separation into the two phases is most efficiently carried out by spinning during in step (ii.b) above, i.e. microconduit I (17) comprises an upper extreme (22) that is above (not shown) the upper liquid level I in the upstream microcavity (4) with valve I (24) placed upstream of the extreme and below upper liquid level I. In other variants of unit A, the actual separation into the two phases is taking place between steps (i) and (ii) by spinning the device at a spin speed that is below the spin speed required for liquid to pass through valve I (24) but typically higher than the spin speeds used in step (i) and many times also higher than the spin speed used in step (iii). In this latter variant of the method, microconduit I (17) preferably has an upper extreme (22) that is below upper liquid level I with valve I (24) placed upstream of the extreme (22) and at a level that is below upper liquid level I. The centrifugal separations described in this paragraph may be applied to (1) reaction mixtures obtained by reacting dissolved reactants with a reactant immobilised to a suspended solid phase in particulate form, (2) samples containing cells or parts of cells, such as cell culture supernatants, cell homogenates, tissue homogenates, whole blood, etc, See also the description and use of unit E.

B. Functional Unit Comprising a Capillary Valve in an Upwardly Directed Microconduit This unit comprises a liquid transport microconduit I (17) with an inlet end (16) and an outlet end (18) and between the ends a capillary valve I.

The characterizing feature is that microconduit I (17) comprises an upwardly directed section (23a) that extends over a part of or over the full length of microconduit I (17). In the preferred variants capillary valve I (24) is present in an upward section (23a).

This innovative microconduit is part of a microchannel structure (2) in a microfluidic device (1). The device, the microchannel structure and the unit are typically designed to permit spinning about a spin axis (3) to create a force, for instance centrifugal force and/or hydrostatic pressure, that will drive a liquid aliquot abutting the upstream side of valve I (24) to pass through the valve for further transport and processing in parts of the structure that are downstream of valve I (24). Capillary force in the form of self-suction may be used as a supplement for the transport, for instance during non- or low-spinning conditions and in particular in order to transport a liquid aliquot or its front meniscus from a lower level to an upper level and/or from a liquid inlet port to a first valve position of a microchannel structure (port=opening in the surface of the device). The unit may also be present in a microfluidic device in which forces other than the ones mentioned are utilized in the transport of liquid through valve I and/or in or between different parts of the microchannel structure. Typical such other forces are gravitational force of earth, etc.

Inlet end (16) of microconduit I (17) is typically at a higher level than the outlet end (18) which does not exclude that in some variants it may be the other way round with outlet end at the higher level and the inlet end at the lower level.

Microconduit I (17) may be directed continuously upwards or may contain two or more sections that alternating are directed continuously upwards or continuously downwards. The inlet end (16) and/or the outlet end (18) may be part of an upward section, a downward section or a horizontal section. The term "horizontal" means that the section all along is at a constant level which for centrifugal based systems means at an essentially constant radial distance (arc-shaped) including a straight line that has a tangential/orthogonal direction relative to a radius going through centre of the section. The angular length of a horizontal section, if any, is $\leq \pi/20$ radians or $\leq \pi/40$ radians or $\leq \pi/80$ radians. "Continuously upward" and "continuously downward" includes that a section may contain a stretch (=part of a section) that is "horizontal". Horizontal sections may be present between an upward and a downward section. An upward and a downward section (23a, 23b) that are next to each other possibly with a horizontal section between them typically form an upward or a downward turn ("elbow") with an upper extreme (22) or a lower extreme, respectively. In preferred variants microconduit I (24) is shaped as an upward turn with its inlet end (16) at a level that is above or below the level of its outlet end (18), possibly with a horizontal section at one or both of its ends.

Capillary valve I and other capillary valves in unit B may be of the same type as in unit A. See unit A and General about Microfluidic Devices, Background Technology and publications cited in these parts of the specification. In preferred embodiments capillary valve I may be a finger valve as defined for unit C.

Capillary valve I (24) is preferably placed in an upward or a horizontal stretch, if present, of an upward section (23a) and/or at a level that is equal to or above the level of inlet end (16). This upward section (23a) may be part of an upward turn with an upper extreme and the outlet end (18) of microconduit I (17) at a lower level than the inlet end (16). In the case microconduit I (17) contains a downward section, for instance with outlet I (18) at a lower level than inlet end (16), capillary valve I (24) may be placed in the downward section at a level above or below the level of inlet end (16).

Microconduit I (17) may also comprise one or more additional capillary valves, for instance a valve (25) at the inlet end (16) of microconduit I (17) provided that capillary valve I (24) is positioned within microconduit (17). See further unit D but also units A and C.

The inlet end (16) of microconduit I (17) may be connected to an upstream microcavity I (4) that may be a) separation microcavity e.g. of the type described for units A and E, b) a volume-metering microcavity (4a), e.g. of the type discussed for unit A and in WO 02074438 (Gyros AB) with a valve corresponding to valve I associated with the liquid outlet that is used for controlling downstream transport of a metered aliquot, c) a liquid retaining microcavity, such as a mixing and/or reaction microcavity e.g. of the types suggested in WO 2003018198 (Gyros AB), WO 2005094976 (Gyros AB), PCT/SE2005/001887 and U.S. Ser. No. 11/301,165 filed in the name of Gyros Patent AB Dec. 12, 2005 "Microfluidic Assays and Microfluidic Devices"), etc with one, two or more inlet functions with or without a valve between an inlet function and the microcavity and a valve (corresponding to valve I) at its liquid outlet, d) a reaction microcavity of the type described in WO 02075312, i.e. having one or more liquid inlet, each of which may or may not be associated with a valve, and a liquid outlet that is associated with a flow restriction that control liquid flow through the microcavity and/or a valve in a liquid inlet, e) etc.

Retaining microcavities in general are described in WO 03018198 (Gyros AB), for instance. Flow restriction means includes a narrow and relatively long outlet microconduit, a porous bed and membranes in the reaction microcavity etc. See WO 02075312 (Gyros AB) and WO 03024598 (Gyros AB). Capillary valves are preferred with finger valves, for instance of the innovative kind described in this specification, being preferred at outlet functions of reaction microcavities, separation microcavities and mixing microcavities.

The inlet end (16) of microconduit I (17) may alternatively be a) a part of a microconduit branching that comprises two or more inlet and/or outlet ends of other microconduits that are intended for liquid transport, or b) directly or indirectly connected to a liquid inlet port of the microchannel structure (i.e. an opening in the surface of the device containing the microchannel structure containing the unit).

The outlet end (18) of microconduit I (17) may be directly connected to a downstream microcavity II (20) that may be a reaction microcavity, a separation microcavity, a volume-defining unit/volume-metering microcavity etc as discussed for units A and E and for the upstream microcavity (4) in the preceding paragraph with the proviso that microconduit I (17) is part of a liquid inlet function of microcavity II (20).

The outlet end (18) of microconduit I (17) may alternatively be a) part of a microconduit branching that comprises two or more inlet and/or outlet ends of other microconduits that are intended for liquid transport, or b) directly or indirectly connected to a liquid outlet port of the microchannel structure (i.e. an opening in the surface of the device containing the microchannel structure containing the unit).

One inventive aspect related to unit B is a method for transporting liquid in a microchannel structure that comprises this unit and is present in a microfluidic device. This method comprises the steps of:

i) providing a microfluidic device in which there is a microchannel structure (2) that comprises unit B, typically with an upstream microcavity (4) connected to the inlet end (16) of microconduit I (17), and with none, one, two or more capillary valves upstream of capillary valve I (24) in microconduit I (17) and with a front meniscus of an aliquot of a liquid at the first capillary valve in microconduit I (17) and a rear meniscus placed upstream of the inlet end (16) typically at a level above the level of valve I (24), ii) moving the front meniscus successively across the capillary valves of microconduit I (17) that are upstream of capillary valve I (24) by applying a driving force on the liquid aliquot and halting the front meniscus at capillary valve I (24), with the proviso that this step is only carried out if there are one or more capillary valve(s) upstream of capillary valve I (24) in microconduit I (17), iii) moving the front meniscus across capillary valve I (24)
   a) subsequent to step (i) if no capillary valve is present upstream capillary valve I (24) (i.e. capillary valve I is the first capillary valve in microconduit I), or
   b) subsequent to step (ii) if said one or more capillary valves are present in microconduit I,
   by applying sufficient driving force on the aliquot when the front meniscus is to be forced across a capillary valve, iv) moving at least a part of the aliquot to a part of microconduit I (17) that is downstream of capillary valve I (24) and typically also downstream of the outlet end (18) of microconduit I (17) by applying a sufficient driving force on the aliquot to bring it at least across capillary valve I.

The rear meniscus in step (i) is typically a meniscus of the same aliquot as the front meniscus. The rear meniscus is typically present in the upstream microcavity (4) (if present).

In the most common variants there are no capillary valves upstream of capillary valve I (24) in microconduit I (17). If such a capillary valve(s) is/are present then one of them is preferably located to the inlet end (16) of microconduit I (17).

Preferred variants also encompass that the microfluidic device (1) provided in step (i) is capable of being spun about a spin axis (3) such that centrifugal force possibly combined with hydrostatic pressure created within the structure during spinning is capable of creating a driving force that pushes the front meniscus across the capillary valve(s) in microconduit I (17) (step (ii) and/or step (iii)) and the downstream transportation between the valves (in step (ii)) and after capillary valve I (24) (step iv). The combination with hydrostatic pressure are important for valve(s) that is/are placed within an upward section (23a) for instance encompassing the inlet end (16) of microconduit I (17). Capillary force may be used as an alternative and/or as a supplement to centrifugal force to reach the next subsequent capillary valve after one valve has been passed, or for downstream transportation once the last capillary valve in microconduit I (17) has been passed, for instance capillary valve I (24), such as in step (iv). The latter downstream transportation in particular applies if the upward section (23a) is part of an upward turn that has an upper extreme (22) that is above the initial rear meniscus or upper liquid level I in the upstream microcavity (4) such as above the uppermost part (7) of the upstream microcavity (4). See unit A.

In certain variants of the method aspect, microconduit I (17) has an upward turn and valve I (24) in the upward section (23a) of the turn. It is then advantageous to form a continuous liquid plug from valve I (24) with the front meniscus in the downward section, such as below the level of the rear meniscus in the upstream microcavity (4) and/or below upper liquid level I of the uppermost part (22) of the turn and/or below the level of the inlet end (16) of the microconduit I (=liquid outlet (6) of the upstream microconduit (4)). This liquid plug will assist in the transportation such that the spin speed can be reduced once the front meniscus has passed the highest level/upper extreme (22) of microconduit I (17). For details see unit A.

Unit C. Capillary Stop Function (Finger Valve, Finger Vent Etc)

This unit comprises a microconduit I (17) with an inlet end (16) and an outlet end (18) and a capillary stop function. Depending on design and position within a microchannel structure, microconduit I (17) can be used as a liquid transport microconduit or a vent microconduit A segment (46) of microconduit I (17) defines a capillary stop function (24) by containing a sharp change in geometric surface characteristics such as a sharp change in a cross-sectional dimension (lateral change, not shown), and/or a sharp increase in non-wettability in chemical surface characteristics. The change and/or increase are typically local (44a or 44b) within the microchannel structure in the sense that the segment (46) may have a certain length encompassing the whole of microconduit I or a part thereof. The segment thus encompasses none, or either one or both of the ends of microconduit I. For increases in non-wettability characteristics this means that at least one, two or more of the inner walls of the microconduit comprises this kind of change as described in Background Technology, General about Microfluidic Devices and publications referenced in these parts of the specification.

Inlet end (16) of microconduit I (17) is typically at a higher level than outlet end (18) which does not exclude that in some variants it may be the other way round with outlet end (18) at the higher level and inlet end (16) at the lower level.

The capillary stop function of this unit has two different primary uses: a) a vent solely for inlet or outlet of gas/air, and b) a stop/flow valve for liquid transported through the microconduit. Use (a) contemplates that the inlet end (16) of microconduit I is intended to be in contact with liquid while the outlet end (18) shall only be in contact with air/gas. Use (b) contemplates that both ends are to be in contact with liquid, successively and/or concomitantly.

The characterizing feature is that at least a part of the segment is divided into two or more microchannels (fingers) (42) and the inventive capillary stop function (24) is therefore a finger valve or a finger vent. The inner surface area defined by the change in surface characteristics is present within the microchannels (42) or abutted to or covering the inlets (45)

and/or the outlets (43) of the microchannels (42). Sharp changes in geometric surface characteristics include e.g. sharp increases in a lateral cross-sectional dimension defined by the inlet ends (45) or the outlet ends (43) of the microchannels (42). An inner surface area of increased non-wettability (44*a*) may start and/or end at the inlet ends (45) and/or the outlet ends (43) of the microchannels (42) and/or may be completely within the microchannels and/or cover either one (44*b*) or both of the inlet ends (45) and the outlet ends (43) of the microchannels (42). The area of increased non-wettability may be divided into two or more subareas associated with the same stop function, for instance one subarea at the inlet ends of the microchannels and another one at the outlet ends of the same microchannels. The inner surfaces of the microchannels between two such subareas are typically wettable. Abutment or coverage of only the inlets (45) or only the outlets leaving the opposite ends hydrophilic often gives advantages (see below).

The segment (46) defined above in the innovative capillary stop function (24) extends between
a) the most upstream of the upstream ends (45) of the microchannels (42) and the upstream end (47) of the non-wettable surface area (44*a* or 44*b*), and
b) the most downstream of the downstream ends (43) of the microchannels (42) and the downstream end (48) of the non-wettable surface area (44*a* or 44*b*).

The number of microchannels (42) is typically two, three, four, five, six or more with an upper limit typically being fifteen, twenty, thirty, fifty or more. At least two of the microchannels in a capillary stop function of the invention are functionally equal in the sense that a) no liquid passes through any of the microchannels when the function is a pure vent, and b) liquid can pass through at least two, such as all, of the microchannels in parallel when the function is a stop/flow valve (in fact essentially in parallel since a time variation for break through between the microchannels from 0 up to 15 seconds at use may be acceptable). This includes that the individual microchannels (42) in essence should have the same shape with respect to one or more features, selected amongst length, curvature, and cross-sectional dimensions like depth, width, area etc, longitudinal variations etc. The microchannels (42) of a capillary stop function of the finger type are thus distinct and well-defined in the sense that they are not random pores with a spectrum of directions and intersections as in conventional porous plugs, beds, membranes and filters.

The area of changed surface characteristics may partially or completely cover microconduit I (17), e.g. start at, before or after the inlet end (16), and/or end at, before or after the outlet end (18) of microconduit I.

The length, depth and width of a microchannel (42) depend among others on the stop function being a valve or a vent, the size and form of cross-sectional dimensions of the microconduit before and/or after microchannels, cross-sectional dimensions of the individual microchannels, desired flow rate before or after the microchannels, desired driving force including spin speed for centrifugal based devices, position on the device, fabrication technique etc.

The lengths of individual microchannels (42) may be different or equal for two or more, such as all, of them. Typical lengths of a microchannel are 0.1, such as 0.5 or 0.75 or 1 or 3 or $\geq 5$ or $\geq 10$, and/or $\leq 10^2$ or $\leq 10^3$ or $\leq 10^4$ or $\leq 10^5$, times the largest of its width and depth of the microchannel. In the case the width and depth varies along the length of a microchannel then the comparison is with the largest width and largest depth. In absolute figures typical lengths are found in the intervals $\geq 5$ µm, such as $\geq 10$ µm $\geq 50$ µm $\geq 100$ µm or $\geq 500$ µm or $\geq 1\,000$ µm or $\geq 3\,000$ µm, and/or $\leq 50\,000$ µm, such as $\leq 25\,000$ µm or $\leq 10\,000$ µm or $\leq 5\,000$ µm or $\leq 1\,000$ µm.

The depth and/or width are typically different or equal for two or more, such as all, of the microchannels (42). In absolute figures typical depths and/or widths are $\geq 1$ µm, such as $\geq 5$ µm $\geq 10$ µm or $\geq 20$ µm $\geq 50$ µm, and/or $\leq 500$ µm, such as $\leq 200$ µm or $\leq 100$ µm or $\leq 50$ µm or $\leq 20$ µm.

In the case the microchannels (42) are shorter than microconduit I, the sum of the open cross-sectional areas ($A_{sum}$) of the microchannels (42) at their upstream end (45) and/or their downstream end (43) is equal to or larger or smaller than the open cross-sectional area of the microconduit (42) immediately before and/or after the segment ($A_{before}$, $A_{after}$). The ratio $A_{sum}/A_{before}$ (and/or $A_{sum}/A_{after}$) is typically in the interval $\geq 1$, such as $\geq 2$ or $\geq 5$ or $\geq 10$, and/or $\leq 1$, such as $\leq 0.5$ or $\leq 0.2$ or $\leq 0.1$. In the case of different depths and/or widths at a certain position the intervals refer to the largest depths and largest width at the position. Compare with trapezoidal or triangular cross-section.

In valve variants of unit C, the inlet end (16) and/or the outlet end (18) of microconduit I (17) is typically part of a branching or connected to a microcavity as described for units A, B and E. The inlet end (16) of may alternatively be directly or indirectly connected to an inlet port and the outlet end of the same microconduit similarly to an outlet port. In principle any combination of functionalities as referred to in different parts of this specification may be associated with microconduit I in a form comprising the inventive finger valve after the appropriate adaptation.

In vent variants of unit C (not shown), the inlet end of microconduit I is typically directly linked to a microcavity intended to contain liquid or a microconduit to be used for the transport of liquid. The outlet end of microconduit I is then in direct or indirect communication with ambient air, possibly via one or more air/gas microconduits, and/or with other parts of the same microchannel structure or with parts of other microchannel structures on the same microfluidic device. This other parts are also contemplated as microcavities/microconduits for air/gas. The innovative finger vent function is preferably located to the inlet end of microconduit I, or alternatively microconduit I comprises an additional capillary stop function that is placed at this position. This additional capillary stop function may or may not be a finger vent.

Microconduit I (17) may downstream or upstream of a finger function (24) contain a section that have a larger or smaller cross-sectional area than on the other side of the function, preferably with a smaller cross-sectional area downstream of the function than upstream thereof. This in particular applies if the finger function is a finger valve. Compare unit A.

Microconduit I (17) may contain one or more additional capillary valves. One (25) of these extra valves is preferably placed upstream of the finger valve (24) and then preferably located at the inlet end (16) as described for the other innovative units of this specification (in particular unit D). One or more of these additional capillary valve(s) may be a finger valve or a capillary valve of the kinds described in Background Technology, General about Microfluidic Devices and publications referenced in these parts of the specification.

An interesting finger valve may be accomplished if the innovative finger valve
a) is placed at the outlet end (16) of microconduit I (17), typically extending from the inlet end (16) to the outlet end (18) of microconduit I (segment (46)=microconduit (17)), or b) its non-wettable area (43*a*) is abutted to or is covering the upstream ends (47) of the microchannels (42) but not the downstream ends (48) of the same microchannels, and the downstream ends of the microchannels are in fluid communication with means that permits selective wetting of the interior of the microchannels from this end of microconduit I/the microchannels.

A particular preferred variant of (a) comprises that valve I (=the segment) and microconduit I coincide and that the inlet end of valve I/microconduit I is directly attached to an upstream microcavity and the outlet end of valve I/microconduit I is directly attached to a downstream microcavity. Both these microcavities can be selected as outlined for the upstream microcavity (4) and the downstream microcavity (20) of unit A. See above.

For variant (b) above the term "means for selective wetting" includes a) a downstream microcavity that has a wetting inlet in fluid communication with the outlet end of microconduit I, and b) that the outlet end of microconduit I is part of a branching that comprises the end of a microconduit in which liquid can be provided separately to the downstream end of the microchannels. When liquid is provided via this kind of wetting means, liquid will be sucked into the hydrophilic microchannels up to the non-wettable part. One can envisage that this kind of valves will require an increased liquid pressure for breakthrough in the downstream direction and therefore make them suitable for use in outlet ends of reaction microcavities, mixing chambers and other retaining microcavities in which liquid is to be retained under pressure. For various kinds of microcavities see General about Microfluidic Devices.

Microconduit I (17) of unit C may have one or more upward sections (23*a*) as described for unit B, preferably with the finger valve (24) in at least one of these sections. The upward section (23*a*) may be part of an upward turn as described elsewhere in this specification. Microconduit I may also have other shapes as discussed for units A-B.

One inventive aspect related to unit C is a method utilizing a microfluidic device in which there is a microchannel structure comprising this unit. This method is a method for transporting a liquid across the capillary stop function of unit C. The method comprises the steps of:

i) providing a microfluidic device in which there is a microchannel structure that comprises unit C as defined above with a front meniscus of an aliquot of a liquid at a position upstream of the capillary stop function (24) and a rear meniscus placed upstream of the inlet end (16) typically at a level above the level of the capillary stop function (24), and ii) moving the front meniscus
  a) to and across the capillary stop function if the function is a valve, possibly by first halting and then resuming movement the front meniscus at the stop function, or
  b) to the function if the function is a vent
  by applying a driving force The rear meniscus in step (i) is typically a meniscus of the same aliquot as the front meniscus. The rear meniscus is typically present in the upstream microcavity (4) (if present).

The driving force in steps (i) and (ii) may be air/gas overpressure or hydrostatic pressure applied to a rear meniscus of the aliquot, centrifugal force etc. The transport/moving to the capillary stop function (24) may also utilize capillary force. Passing across the capillary stop function (24) typically require an active increase in driving force which means that the driving force can be selected amongst the same forces as for the initial moving with exclusion of capillary force that is not suitable. If the device is designed for utilizing centrifugal force, an increased spinning is preferred. After step (ii) other driving forces or combination of forces than in step (ii) may alternatively be used for bringing the aliquot or a part of it further downstream into the microchannel structure. Centrifugal force may for instance be replaced with and/or supplemented with capillary force and/or hydrostatic pressure. In the case the finger valve is linked to or is part of any other of the units A-F, steps (i) and (ii) are accordingly adapted to the requirement of the steps of the corresponding method.

Unit D. Protected Capillary Valve Unit.

This unit comprises a liquid transport microconduit I (17) with an inlet end (16) and an outlet end (18) and comprising a capillary valve I (24).

The characterizing feature is that the microconduit comprises one or more additional capillary valves (25). Capillary valve I (24) is preferably a finger valve, typically as defined for unit C, with one or more of the additional valves placed upstream of valve I. An additional capillary valve may also be a finger valve or of the kinds discussed elsewhere in this specification for other units, in Background Technology, in General about Microfluidic Devices and in publications referenced in these parts. One of the additional valves (25) is preferably placed at the inlet end (16) of microconduit I (17) with the proviso that valve I (24) then is placed within the microconduit.

This innovative microconduit I (17) is part of a microchannel structure in a microfluidic device of the same kind as discussed for unit A-C and E-F.

Inlet end (16) of microconduit I (17) is typically at a higher level than the outlet end (18) which does not exclude that in some variants it may be the other way round with outlet end (18) at the higher level and inlet end (16) at the lower level.

As described for units B and C, microconduit I (17) may contain one or more upward sections (23*a*) and/or one or more downward sections (23*b*) and/or one or more horizontal sections, one or more upward turns, one or more downward turns, upper extreme(s) (22) etc. Capillary valve I, such as in the form of a finger valve, may be present in any of these parts, most typically in an upward or a downward section of an upward turn with due care taken for the desired function in each particular case. For details see units B and C.

The inlet end (16) or the outlet end (18) of microconduit I (17) in unit D is typically part of a branching or connected to a microcavity as described for units A, B, C and E. The inlet end (16) of microconduit I may alternatively be directly or indirectly connected to an inlet port and the outlet end (18) to an outlet port. In principle any combination of the functionalities referred to may be associated with microconduit I of unit D provided the proper adaptation is made.

One inventive aspect of unit D is related to a method for transporting a liquid in a microchannel structure comprising unit D. This method is applicable also to units B and C if they comprise two or more capillary valves as described above The method comprises the steps of:

i) providing a microfluidic containing a microchannel structure containing unit D;

ii) providing a liquid aliquot abutted to the most upstream of the capillary valves (=valve 1, front meniscus at valve 1);

iii) moving the aliquot or a part thereof (front meniscus) across valve 1 by increasing the driving force and halting the meniscus at the next capillary valve (valve 2), possibly with a decrease in driving force after the meniscus has passed valve 1;

iv) moving the meniscus across valve 2 by increasing the driving force and halting the meniscus at the next capillary valve (valve 3) (if any), possibly with a decrease in driving force after the meniscus has passed valve 2, v) repeating steps (iii) and (iv) until all the capillary valves of microconduit I have been passed, vi) moving the meniscus through the outlet end of microconduit I.

This method also comprises that the rear meniscus is placed as described for the method aspects of unit B and C.

Due to the hydrophilicity of the microconduit (self-section) the driving force can be decreased after passage of each individual capillary valve, i.e. one can rely partly or wholly on capillary transport (passive) between the valves.

In preferred variants the device is adapted for using centrifugal force obtained by spinning the device. Increasing the driving force then means increased spinning. For variants in which unit D is incorporated into any of the other units described in this specification the method above may be adapted to the method given for these units.

As discussed in the context of other units of this specification, microconduit I (17) typically comprises at most two capillary valves (25,24) with the most upstream one (25) being a capillary non-finger valve preferably placed at the inlet end (16) and the subsequent valve (24) preferably being a capillary finger valve.

In preferred variants the inlet end (16) of microconduit I (17) defines an intersection between microconduit I and a transport pathway in which liquid containing material that may lower the efficiency of a capillary valve, which is downstream of the first capillary valve is transported, by-passes the inlet end of microconduit for downstream parts of the pathway. These downstream parts are typically not coinciding with downstream parts of the pathway branching into microconduit I. See discussion of variants of units A-E in which the upstream microcavity (4) that may be present may have a lower part (4b) corresponding to a downstream part of a transport pathway for material that can be harmful for capillary valves, for instance by clogging or by adsorption. Typical harmful materials are discussed in the context of problems overcome by the invention and in the context of particular units.

Unit E. Unit for Separating an Upper Phase Typically a Liquid Phase from a Denser Phase Typically Containing Particulate Material.

The unit comprises:

d) an separation microcavity (4) with a liquid inlet I (5) and a liquid outlet I (6) with the former being at a higher level than the latter, e) a liquid transport microconduit I (17) that has an inlet end (16) directly connected to liquid outlet I (6) and an outlet end (18) that is at a lower level than the inlet end (16) (and liquid outlet I).

The separation microcavity corresponds to the upstream microcavity in unit A. Liquid outlet I (6) is placed at an intermediary level between the level of the lowest part (8) and the level of the top part (7) (uppermost part) of the separation microcavity (4) and defines a lower part (4b) and an upper part (4a) of the microcavity (4).

The separation microcavity (4) is capable of retaining a predetermined liquid volume which defines an upper liquid level I in the microcavity. This upper liquid level is equal to or lower than the level of the uppermost part (7) the microcavity, and above the level of liquid outlet I (6).

The microfluidic device that contains the microchannel structure in which the unit is a part is designed to permit spinning about a spin axis in order to manage a separation of a liquid containing a denser and a lighter material into an upper and a lower phase, and to export the upper phase to downstream parts of the microchannel structure via liquid outlet I (6) and microconduit I (17). The export to downstream parts utilises centrifugal force created by the spinning, and/or hydrostatic pressure built up within the microchannel structure during spinning, and/or capillary force. Other forces may also be used, e.g electrokinetic forces, in combination with one or more the forces just mentioned. See also "General about Microfluidic Devices".

The characterizing feature comprises that:
a) microconduit I (17) is associated with a valve I (24), preferably a capillary valve I, and
b) the flow direction through liquid outlet I (6) is directed upwards, and/or
c) liquid outlet I (6) is placed in an downwardly turned part of an inner wall of the separation microcavity (4), and/or
d) the microconduit part next to the inlet end (16) of microconduit I (17) is directed upwards.

Valve I (24) may be placed within or at the inlet or outlet end (16 or 18) of microconduit 1 and is in most variants so far envisaged preferably a finger valve of the type described for unit C. The cross-sectional dimension of microconduit I should in many variants be larger upstream than downstream of valve I, with a factor e.g. $\geq 1$, such as $\geq 2$ or $\geq 5$ or $\geq 10$. This in particular applies if valve I is a finger valve and/or if creation of a driving liquid height/plug is to be formed in the microconduit when in use. See units A-C.

Microconduit I (17) typically has an upper extreme (22) that preferably is placed either at the inlet end (16) (at liquid outlet I (6)) or internally within the microconduit (upper extreme=elbow directed upwards). This upper extreme (22) may be at the same level as liquid outlet I (6) of the separation microcavity (4) in which case microconduit I in preferred variants has a first short horizontal section followed by a downward section down to the outlet end (18). The upper extreme (22) may alternatively be above the level of liquid outlet I (6), such as above upper liquid level I of the separation microcavity (4) and even above the level of the top (7) of the separation microcavity (4). In these latter variants the upper extreme (22) is typically within a variant of microconduit I (17) that starts with an upward section (23a) followed by a downward section (23b) where the joint between the sections defines the upper extreme (22). This kind of upper extreme may comprise a horizontal section between the upward and downward sections. In the variants of this paragraph, valve I (24) is typically placed at or if possible upstream of the upper extreme (22) (i.e. in the upstream section (23a)) and above or below upper liquid level I, such as above 25% of the height between the inlet end (16) and the upper extreme (22). The preferred relative position of the valve within the upstream section (23a) is preferably even higher, such as above 50% or above 75% of the height between the inlet end (16) and the upper extreme (22).

In one of the most preferred variants valve I (24) is placed in an upward section (23a), and below the level of upper liquid level I and the upper extreme (22). Filling a predetermined volume of liquid into the microcavity (4) will place a rear meniscus at upper liquid level I and a front meniscus at the first valve in the microconduit (17), such as at valve I (24) if only no additional valve as described elsewhere in this specification is present. Subsequent spinning of the device will equilibrate the rear and front meniscuses to the same level and above the level of valve I (24). By slowing down the spinning capillary force will take the front meniscus over the upper extreme (22) whereafter resumed high spinning will quickly empty the upper part (4a) of the separation microcavity (4) down to the level of liquid outlet I (6). As for unit A the spinning speed can be reduced during emptying if a continuous liquid plug is maintained while the front meniscus is moving downwards. This includes that dimensions, shapes inner volumes etc of the separation microcavity (4) and microconduit I (17) are properly adapted to each other. See also the description of units A-C and the corresponding method aspects in which also other relative positions are given.

Valve I (24) may also be placed downstream the upper extreme.

Microconduit I (17) may also contain an extra valve (25) placed upstream of valve I (24), in particular if valve I (24) is a capillary finger valve or some other kind of valve that has a tendency to be clogged or otherwise harmed by the liquids used, This extra valve is preferably placed at the inlet end (16) of microconduit I (17) and selected to be less prone to be harmed by the liquids used. This variant may also be useful in the case microconduit I (17) contains downward turns or other shapes that promotes collection of particulate material and liquids at positions upstream of valve I (24).

See units A-D for alternative shapes of microconduit I and positioning of valves within microconduit I.

Capillary valves in the unit, such as valve I (24), are typically based on a change in chemical and/or geometric inner surface characteristics in a hydrophilic flow path of the unit according to principles that are well-known in the field. The change may be as a sharp increase in cross-sectional dimension of a microconduit (lateral change) and/or a sharp increase in non-wettability of an inner surface of a microconduit, in both cases in the flow direction. The change is typical local (break), for instance a non-wettable/hydrophobic surface break in an otherwise hydrophilic flow path. The inner non-wettable surface may be roughened and/or expose fluorohydrocarbon groups. See further under Background Technology and General about Microfluidic Devices and the publications referenced under these headings.

The liquid flow starting to exit through liquid outlet I (6) may have various directions in relation to the centrifugal force at liquid outlet I (6). The flow direction may thus comprise (a) an upward/inward component (inward radial component), or (b) essentially tangential (horizontal). The flow direction relative to the direction of the centrifugal force at liquid outlet I (6) may thus be for alternative (a) at least partially against the centrifugal force, and for alternative (b) essentially orthogonal against the centrifugal force. Expressed as an angle ($\alpha$) relative to the direction of centrifugal force at liquid outlet I this may be for alternative (a) $90° \leq \alpha \leq 270°$, such as $95° \leq \alpha \leq 265°$ (against), and for alternative (b) $90° \leq \alpha \leq 100°$, such as $90° \leq \alpha \leq 95°$, and/or $260° \leq \alpha \leq 270°$, such as $265° \leq \alpha \leq 270°$ (orthogonal)

The angle ($\alpha'$) between the centrifugal force at liquid outlet I (6) and the inner wall around liquid outlet I (6) may be for alternative (a)-$90° \leq \alpha' < 0°$ and/or $0° < \alpha' \leq 90°$, such as -$90° \leq \alpha' \leq -5$ and/or $5° \leq \alpha' \leq 90°$, and for alternative (b)-$10° \leq \alpha' \leq 10°$, such as $-5° \leq \alpha' \leq 5°$ or in particular $\alpha'=0°$. The direction of the inner wall and/or of the corresponding opening in alternative (b) essentially coincides with the direction of the centrifugal force.

The part of microconduit I (17) that is next to liquid outlet I (6) of the separation microcavity (4) preferably has a direction selected amongst the main directions for flow through this liquid outlet although the two directions do not need to be the same.

Liquid outlet I (6) divides the separation microcavity (4) in a lower part (4b) and an upper part (4a) as discussed for unit A above. In typical cases the lower part (4b) constitutes $\geq 10\%$, such as $\geq 25\%$ or $\geq 50\%$ or $\geq 70\%$ or $\geq 80\%$ of the total volume of the separation microcavity (4). The exact relative volumes of the parts are determined by the relative volumes of the phases obtained after their formation by spinning of the device. It is often important that the lower part (4b) should have at least the same volume as the lower phase. Thus the lower surface of the phase to be exported through liquid outlet I (6) should be below the level of this outlet, e.g. by leaving a liquid height between this lower surface and liquid outlet I (6)$\geq 10$ µm$\geq 50$ µm$\geq 100$ µm$\geq 200$ µm.

The separation microcavity (4) may be tapered towards the level of an inlet (5) and/or an outlet (6) or towards this inlet and outlet as such. Tapering typically means that at least one, two or more of the inner walls at the outlet/inlet concerned form an acute angle ($\beta \leq 90°$) with the main flow direction through the tapering or with a straight line (radius) going from the spin axis towards the outlet concerned. This angle ($\beta$) preferably is within the interval of 10-60°, more preferably 20°-40°, such as 25°-35° with preference for about 30°. These intervals are applicable also to pure vent outlets. With respect to liquid outlets and pure vent outlets tapering will counteract air bubble formation during filling of the microcavity with liquid.

The separation microcavity (4) may be constricted at the level of liquid outlet (6). This constriction may be defined by the tapering discussed in the preceding paragraph.

The constriction and/or tapering means that the largest cross-sectional area of the microcavity, or of an upper and/or lower part thereof typically is larger than the cross-sectional area at the level of the outlet/inlet concerned with a factor >1, such as $\geq 1.25$ or $\geq 1.5$ or $\geq 3.0$ or $\geq 5.0$.

In preferred designs the cross-sectional area in the upstream microcavity is typically larger upstream of liquid outlet I (6) than in microconduit I (17), e.g. with a factor $\geq 1$, such as $\geq 2$ or $\geq 5$ or $\geq 10$.

Additional details about tapering and constrictions are given for unit A.

The lower part (4b) of the separation microcavity (4) is typically communicating with one or more outlets (14) to ambient atmosphere solely for venting out air displaced by liquid entering this part. The actual opening (14) (vent outlet port) in the surface of the device for an outlet of this kind is preferably located at a higher level than liquid inlet I (5) and typically also at a higher level than the corresponding actual inlet opening (9) in the surface of the device through which liquid is initially introduced (liquid inlet port). There may be a capillary stop function (15a) (downstream end) associated with this kind of outlet(s), in particular if the corresponding vent outlet opening (14) in the surface of the device is at a lower level than the liquid inlet (5) of the upstream microcavity (4). It follows that the separation microcavity (4) may form a U-shaped or downward turn microcavity. In the case there are several vent outlet openings (14) in the downstream part (4b) of the microcavity, this part (4b) may be divided into two or more fingers (finger microcavity).

The upper part (4b) of the upstream microcavity (4) may be used as a volume-metering microcavity, if there for instance is an overflow opening (10) at the level of liquid inlet I (5).

See below. This metering is likely to be more accurate if the capillary stop function (15a) associated with a vent outlet function (14) of the type discussed is placed at a lower level than liquid outlet I (5). The capillary stop function (15a) preferably is a finger vent as described for unit C. See also unit A for further details.

The lower part (4b) may also have a liquid outlet I' for export of material from the lower part after the upper part has been emptied via liquid outlet I (not shown). In this case liquid outlet I' is at a lower level than liquid outlet I.

The upper part (4b) of the separation microcavity (4) may be part of a volume-defining unit, for instance of the type outlined for the upstream or downstream microcavity of unit A or in WO 02074438 and WO 03018198 (both of Gyros AB). In short this typically means that liquid inlet I (5) is connected to an inlet microconduit I (8a) in which there is an overflow opening (10) at the same level as liquid inlet I (5). The overflow opening (10) is connected to a downwardly directed overflow microconduit (11) through which excess liquid added through the inlet microconduit can be selectively discarded by the proper spinning of the device.

The upper part (4b) may also contain one or more additional liquid inlets as indicated for unit A.

The outlet end (18) of microconduit I (17) may be directly connected to a downstream microcavity (20) of the kinds and functions indicated for unit A.

The relative dimensions of microconduit I (17) and the separation microcavity (4) including liquid inlets, outlets, vents, valves etc and their positions are preferably adapted for creating a driving plug height in microconduit I as outlined for unit A.

The inventive aspect of unit E comprises also a microfluidic method for the centrifugal fractionation of an aliquot of liquid containing denser and less dense material into a less dense upper phase and a denser lower phase, and thereafter transporting at least a part of the upper phase to downstream parts of the same microchannel structure as in which the separation is taking place. The method is in principle comprised within those variants of the method described for unit A which permit sufficient spinning to allow for centrifugal fractionation of the liquid in the upstream microcavity into a denser lower phase and a less dense upper phase without contaminating microconduit I with material that after the separation is in principle found exclusively in the lower phase. The method aspect of unit D includes also further processing of the upper aliquot transported downstream, such as mixing for diluting, mixing with other aliquots comprising reactants, performing reactions such as biological reactions that are included in assay protocols like enzyme assay protocols, affinity assay protocols etc. These assay protocols may involve heterogeneous reactions such as in heterogeneous enzyme assays, heterogeneous non-competitive assays such as sandwich assays, heterogeneous competitive assay etc and the corresponding homogeneous reactions and assay protocols. The assay protocols are typically carried out for characterization of an uncharacterized entity in a sample, such as for the quantitative or qualitative determination of the amount of an analyte.

F. Detection Unit.

Unit F is part of microchannel structure in which there is a detection microcavity (49) which in the upstream direction is attached to an inlet microconduit for transport of liquid (35) (transport microconduit) to the detection microcavity (49). The detection microcavity is used for detecting the result of a reaction taking place in the detection microcavity or in a reaction microcavity (20) that is positioned upstream of the detection microcavity (49). Centrifugal force is used for transporting liquid between and through the microcavities. The characterizing feature comprises that the detection microcavity (49) comprises a detection microconduit that has an inlet part (36) and an outlet part (32) and therebetween an upward or a downward meander (39).

A meandering microconduit (39) is illustrated in FIG. 4. It comprises a plurality of consecutive returns ($r_1, r_2, r_3, r_4, r_5, r_6, r_7, r_8 \ldots$) with an intermediary section ($r_{1-2}, r_{2-3}, r_{3-4}, r_{4-5}, r_{5-6}, r_{6-7}, r_{7-8} \ldots$) between two neighbouring consecutive returns ($r_1, r_2; r_2, r_3; r_3, r_4; r_4, r_5 \ldots$) anywhere along the meander. The longitudinal position for the returns and the intermediary sections is increasing in the longitudinal direction of the meander (main flow direction of the meander) while the latitudinal position for the returns is alternating around a latitudinal center that may be common for the whole meander or only for a part thereof that comprises two or more consecutive returns. The flow direction in every second intermediary section (=direction of the section) ($r_{1-2}, r_{3-4}, r_{5-6}, r_{7-8}, \ldots$ or $r_{2-3}, r_{4-5}, r_{8-9} \ldots$) is either to the left or to the right while for every pair of two consecutive intermediary sections ($r_{1-2}, r_{2-3}; r_{2-3}, r_{3-4}; r_{3-4}, r_{4-5}; \ldots$) the flow direction in a first section is to the left or to the right while the flow direction in the second section is the opposite (alternating lateral direction of the intermediary sections). Right and left is relative to the main direction of the meander.

In centrifugal based systems downward and upward meanders means that the main direction of flow through the meander contains a component that is towards or along, respectively centrifugal force. In other words the first return is typically above the level of the last return for a downward meander and vice versa for an upward meander. A downward and an upward meander may in preferred cases be vertical by which is meant that the main direction of the meander (longitudinal direction) coincides with the direction of centrifugal force. See FIG. 4 that illustrates a vertical meander that is directed upwards.

At the priority date, typical meanders have a main flow direction that for upwards meanders form an angle $\gamma$ with centrifugal force that is in the interval $145° \leq \gamma \leq 225°$ and for downwards meanders form an angle $\gamma$ which is in the interval $-45° \leq \gamma \leq 45°$. With respect to vertically upward and vertically downward meanders ($\gamma$ is 180° and 0°, respectively), the upward one is preferred primarily because it more easily result in compact microchannel structures. Compare FIGS. 2 and 4.

In preferred variants the meander comprises two, three, four, five or more returns. The upper limit may vary but typically the number of returns is $\leq 50$, such as $\leq 25$ or $\leq 10$.

In typical innovative meander variants, each intermediary section contains a stretch that is parallel with the corresponding stretch in one or more of the other sections. In preferred variants this parallelism occurs for every second section, with absolute preference for every section as illustrated in FIGS. and 4.

In upwardly directed meanders it may be advantageous when the height position (=longitinunal position) for every second return ($r_1, r_3, r_5, r_7, \ldots$ or $r_2, r_4, r_6, r_8 \ldots$) in consecutive returns ($r_1, r_2, r_3, r_4, r_5, r_6, r_7, r_8 \ldots$), such as for every consecutive return ($r_1, r_2, r_3, r_4, r_5, r_6, r_7, r_8 \ldots$), are increasing in the flow direction. In downwardly directed meanders the height position is decreasing in the flow direction for the corresponding combinations of returns. In the simplest of these variants the increase/decrease along the meander is constant between the first and second return in any pair of consecutive returns ($r_1, r_2; r_2, r_3; r_3, r_4; r_4, r_5 \ldots$) or between the first and third return in any triplets of consecutive returns ($r_1, r_2, r_3; r_2, r_3, r_4; r_3, r_4, r_5 \ldots$).

The detection microcavity (49) may comprise two or more serially linked identical or different forms of two or more meanders (not shown). Thus the detection microconduit may comprise three, four or more meanders with the downstream end of an upstream meander being in liquid communication with the upstream end of the closest downstream meander possibly. The liquid communication is via a linking microconduit part. The longitudinal direction of two meanders that are next to each other may differ, for instance with one being downward and the other upward or the other way round. One, two or more or all of the additional meanders in this kind of detection microcavity are typically downward or upward.

The detection microcavity (49) is typically associated with or capable of being associated with a sensor (not shown) that is capable of detecting a signal that represents the result of the reaction. The sensor may be based on spectrometry, such as fluorometry, chemiluminometry (including biochemiluminometry, calorimetry, nephelometry, absorbance etc, calorimetry, conductonmetry etc. The sensing principle utilized is typically matched with the material between the inner wall of the detection microconduit and the outer surface of the device at the detection microcavity, for instance by consisting of a material that is transparent or translucent for the signal that is to be detected by a detector (sensor) associated with the detection microcavity. This material may thus be translucent or transparent for heat, and/or radiation in the UV-range, IR-range and/or the visible range. The material can in many cases be a plastic material.

Upstream of the detection microcavity (49), such as between the detection microcavity (49) and a reaction microcavity (20) in which the reaction to be monitored by measuring in the detection microcavity, there may be various functionalities for properly processing and/or transporting liquids before entering the detection microcavity. There may thus be a) a routing function that prevents a liquid aliquot that might be harmful for the detection microcavity from passing through the detection microcavity, b) a reaction chamber that comprises agents that are capable of neutralizing or removing disturbing substances from a liquid, b) a stop/flow valve, c) flow restriction functionality that impedes liquid flow through the reaction microcavity etc. These different kinds functionalities are well-known in the field and also described or referenced in this specification. The main function of stop/flow valves and a flow restriction functionality in the innovative unit is to secure proper reaction between reactants and/or other treatments including transport between upstream parts of the microchannel structure and the detection microcavity. Preferred valves are non-closing valves, such as capillary valves. Flow restriction functionalities include porous beds, membranes and the like placed in the reaction microcavity. A narrow and/or long microconduit downstream of the reaction microcavity may also work as a sufficient flow restriction. Inner surfaces of a flow restriction functionality may in a similar manner as a porous bed work as a solid phase for one or more immobilized reactants that are to be used in the desired reaction(s), for instance the inner surfaces of a restriction microconduit or of a porous bed, membrane, plug and the like. A solid phase of the kinds referred to above is preferably a part of the reaction microcavity (20).

Non-closing valves, such as capillary valves are discussed under Background Technology, General about Microfluidic Devices and the publications referenced these parts of the specification. Various flow restriction means or functionalities are given above and in WO 02075312 (Gyros AB) and WO 03024598 (Gyros AB), among others.

A microcavity (20) upstream the detection microcavity may have various geometric forms. It may be an unbranched microconduit with no change in cross-sectional dimension or an enlarged part (microcavity) of a microconduit. It may be a mixing microcavity, reaction microcavity etc and contain one, two or more liquid inlets and allow for mixing of two or more liquid aliquots of the same or different volumes within the microcavity, including diluting. At least one of the aliquots contains one or more reactants to be used for the reaction(s) that takes place in the reaction/detection microcavity (20/49). In the upstream direction every liquid inlet of a microcavity (20) is directly or indirectly linked to a liquid inlet arrangement comprising an inlet port, possibly with an intervening volume-defining unit for one or more of the microconduits in the inlet arrangement. See for instance WO 02074438 (Gyros AB) and WO 03018198 (Gyros AB).

Unit F is typically present in a microchannel structure of a microfluidic device that is capable of being spun about a spin axis thereby creating centrifugal force that can assist in moving liquids through the detection microcavity from upstream parts of a microchannel structure. The transport is typically primarily caused by centrifugal force created by the spinning and/or by hydrostatic pressure built up in the microchannel structure during spinning and/or by capillary force (self-suction). See General about Microfluidic Devices.

The inventive part of unit F also comprises a method comprising detecting in solution a result of a reaction that takes place in the detection microcavity (49) and/or in a reaction microcavity (20) that is upstream of the detection microcavity and present in the same microchannel structure (2) as the detection microcavity (20). This method comprises the steps of:

a) providing a microfluidic device comprising a microchannel structure comprising unit F,
b) transporting a liquid I necessary for the detection into the detection microcavity, said transporting comprises spinning of the device to create centrifugal force that is used for the transportation, and
c) detecting said result in the detection microcavity.

In preferred variants the reaction is part of a process protocol comprising that a meander of the detection microcavity contains liquid II prior to step (iii). Step (iii) then comprises that liquid I displaces liquid II, typically without mixing with each other.

General about Microfluidic Devices.

A microfluidic device is a device that comprises one, two or more microchannel structures in which one or more liquid aliquots in the µl-range, typically in the nanolitre (nl) range, containing various kinds of reactants, such as analytes and reagents, products, samples, buffers and/or the like are processed. Each microchannel structure comprises all the functionalities needed for performing the experiment that is to be performed within the microfluidic device. A liquid aliquot in the µl-range has a volume $\leq$1 000 µL such as $\leq$100 µl or $\leq$10 µl and includes the nl-range that has an upper end of 5 000 nl but in most cases relates to volumes $\leq$1 000 nl, such as $\leq$500 nl or $\leq$100 nl. The nl-range includes the picolitre (pl) range. A microchannel structure comprises one or more cavities and/or conduits that have a cross-sectional dimension that is $\leq$10$^3$ µm, preferably $\leq$5×10$^2$ µm, such as $\leq$10$^2$ µm.

A microchannel structure thus may comprise one, two, three or more functional parts selected amongst:
a) inlet arrangements comprising for instance one or more inlet ports/inlet openings, possibly together with a volume-metering microcavity,
b) microconduits for liquid transport,
c) reaction microcavities/units;
d) mixing units, for instance comprising microcavities as discussed elsewhere in this specification,
e) units for microcavities for separating particulate matters from liquids,
f) units for separating dissolved or dispersed/suspended components in the sample from each other, for instance by capillary electrophoresis, chromatography and the like;
g) detection microcavities/units;
h) waste conduits/microcavities/units;
i) valves;
j) vents to ambient atmosphere;
k) anti-wicking functions;
l) liquid directing functions etc.

A functional part may have two or more functionalities:
1. a reaction microcavity and a detection microcavity may coincide, 2. a volume-metering function may comprise one or more valve functions and a metering microcavity and/or an anti-wicking function,
3. a reaction microcavity may comprise one or more valve functions and/or anti-wicking functions,
4. a passive valve function (capillary valve) based on a non-wettable surface break may comprise also an anti-wicking function etc.

Microcavities such as the upstream and downstream microcavities discussed in this specification including also reaction microcavities, separation microcavities, volume.-metering cavities, mixing microcavities, through-flow microcavities for instance associated with flow restriction means for controlling through flow, and other retaining liquid microcavities etc have volumes selected within the intervals given above. Larger volumes such as $\geq 1$ μl or $\geq 5$ μl or $\geq 10$ μl, but still $\leq 1000$ μl, such as $\leq 100$ μl or $\leq 50$ μl or $\leq 25$ μl are typically contemplated for liquid samples containing an analyte before any concentration within a microchannel structure, diluents, and wash liquids. Thus larger microcavities complying with these ranges are typically located to an upstream part of a microchannel structure and are typically present as a volume-metering microcavity, a separation microcavity for removing (separation) particulates from a sample containing an analyte, a mixing microcavities for diluting or mixing a sample containing an analyte with a diluent or a reagent, a diluent storing and/or metering microcavity, a wash liquid storing and/or metering microcavity etc. Microcavities intended for retaining samples or liquid aliquots containing reagents typically have smaller volumes, such as $\leq 5$ μl or $\leq 1$ μl or $\leq 0.5$ μl or $\leq 0.1$ μl, i.e. in the nl-range.

Any of the microcavities discussed in the context of the innovative units, in Background Technology, this part of the specification, in WO 03018198 (Gyros AB) (retaining microcavities) etc may in principle be present in a microchannel structure/unit of the innovative microfluidic devices in direct or indirect fluid communication with the inlet end (16) or the outlet end (18) of microconduit I (17).

Various kinds of functional units in microfluidic devices have been described by Gyros AB/Amersham Pharmacia Biotech AB: WO 9955827, WO 9958245, WO 02074438, WO 0275312, WO 03018198, WO 03024598 etc and by Tecan/Gamera Biosciences: WO 0187487, WO 0187486, WO 0079285, WO 0078455, WO 0069560, WO 9807019, WO 9853311.

An inlet arrangement typically comprises an inlet port and at least one volume-metering microcavity. There may be one separate inlet arrangement per microchannel structure. There may also be an inlet arrangement that is common to all or a subset of the microchannel structures of the device. This latter arrangement typically comprises a common inlet port and a distribution manifold with one volume-metering microcavity for each microchannel structure of the subset. See for instance WO 02074438 (Gyros AB), WO 03018198 (Gyros AB), WO 03083108 (Gyros AB), WO 2005094976 (Gyros AB) etc. A volume-metering microcavity is typically communicating with downstream parts of the corresponding microchannel structure, e.g. a mixing microcavity, reaction microcavity, separation microcavity etc. Microchannel structures linked together by a common inlet arrangement and/or common distribution manifold define a subset/subgroup of the microchannel structures of the device.

Some inlet arrangements contains a microcavity that has no volume-defining ability but is solely used for initial storage of a liquid aliquot dispensed through an inlet port.

The abovementioned microcavities in inlet arrangements may have an U-shaped forms with lower part directed outwards from a spin axis and equipped with a liquid outlet to which is associated a valve function, typically a capillary valve. The liquid outlet is used for transport of a dispensed aliquot to downstream parts of the microchannel structure to which the inlet arrangement is associated. See for instance WO 0146465 (Gyros AB).

A microcavity, such as a volume-metering microcavity, a mixing microcavity, a reaction microcavity etc typically has a valve or a flow restriction means controlling the flow out of liquid from the microcavity concerned. A valve at this position is typically passive, for instance utilizing a change in chemical surface characteristics at the outlet end, such as a boundary between a hydrophilic and hydrophobic surface (hydrophobic surface break) (WO 99058245 (Amersham Pharmacia Biotech AB)) and/or in geometric/physical surface characteristics (WO 98007019 (Gamera)). See also WO 02074438 (Gyros AB), WO 04103890 (Gyros AB) and WO 04103891 (Gyros AB) for preferred valves that are based on hydrophobic surface breaks. Flow restriction means may be in the form of porous beads, membranes and the like or in the form of relatively long an narrow microconduits (restriction microconduits). See for instance WO 02075312 (Gyros AB) and WO 03024598.

See also WO 02075775 (Gyros AB) and WO 02075776 (Gyros AB).

The microfluidic device may also comprise other common microchannels/microconduits that connect different microchannel structures. Common channels/conduits including their various parts such as inlet ports, outlet ports, vents, etc., are considered part of each of the microchannel structures they are common for.

Each microchannel structure has at least one inlet opening for liquids and at least one outlet opening for excess of air (vents) and possibly also for liquids.

The number of microchannel structures/device is typically $\geq 10$, e.g. $\geq 25$ or $\geq 90$ or $\geq 180$ or $\geq 270$ or $\geq 360$. At least one, preferably two or more, such as all or a subset, of the microchannel structures on a device contain at least one of the innovative units presented in this specification.

A subgroup of microchannel structures comprises microchannel structures linked together by a common functionality such as a common inlet arrangement, which for instance is common for 4-25 microchannel structures. All the microchannel structures of such a subgroup contain essentially the identical unit(s) of the invention (selected from units A-F). Microchannel structures in such a subgroup are typically functionally equivalent, i.e. they can be used in a timely parallel fashion at least with respect to the occurring innovative unit(s).

Different principles may be utilized for transporting the liquid within the microfluidic device/microchannel structures between two or more of the functional parts described above.

Inertia force may be used, for instance by spinning the disc as discussed in the subsequent paragraph. Other useful forces are electrokinetic forces, non-electrokinetic forces such as capillary forces, hydrostatic pressure etc.

A microfluidic device typically is in the form of a disc. The preferred formats have an axis of symmetry ($C_n$) that is perpendicular to or coincides with the disc plane. In the former case n is an integer $\geq 2$, 3, 4 or 5, preferably $\infty$ ($C_\infty$). In the latter case n is typically 2. In other words the disc may be rectangular, such as in the form of a square, or have other polygonal forms. It may also be circular. Once the proper disc format has been selected centrifugal force may be used for driving liquid flow, e.g. by spinning the device about a spin axis that typically is perpendicular to or parallel with the disc plane. Parallel in this context includes that the spin axis coincides with the disc plane. In the most obvious variants at the priority date, the spin axis coincides with the above-mentioned axis of symmetry. Preferred variants in which the spin axis is not perpendicular to the disc plane are given in International Patent Application WO 04050247 (Gyros AB)

For preferred centrifugal-based variants, each microchannel structure comprises an upstream section that is at a shorter radial distance than a downstream section relative to the spin axis. Spinning of the device about this spin axis will then induce transportation of liquid from the upstream section to the downstream section, for instance through microconduit I of units A-E or into the meander of unit F.

The preferred devices are typically disc-shaped with sizes and forms similar to the conventional CD-format, e.g. sizes that corresponds CD-radii that are the interval 10%-300% of the conventional CD-radii (about 12 cm). The upper and/or lower sides of the disc may or may not be planar.

Microchannel structures or parts thereof such as microconduit I of units A-E or the meander of unit F are preferably manufactured from an essentially planar substrate surface that exhibits uncovered microstructures defining at least a part of microconduit I of units A-E or at least part of the meander of unit F and another essentially planar substrate surface exhibiting the remaining part of microconduit I or the remaining part of the meander. The covered form of microconduit I or a part thereof or of the meander or a part thereof is obtained by apposing the two substrate surfaces defining the desired structure together. Compare for instance WO 91016966 (Pharmacia Biotech AB), WO 01054810 (Gyros AB), WO 4050247 (Gyros AB), WO 03055790 (Gyros AB etc. Both substrates are preferably fabricated from plastic material, e.g. plastic polymeric material.

The fouling activity and hydrophilicity of inner surfaces should be balanced in relation to the application. See for instance WO 0147637 (Gyros AB) and WO 03086960 (Gyros AB).

The terms "wettable" and "non-wettable" with respect to inner walls contemplate that the inner surface of an inner wall has a water contact angle $\leq 90°$ or $\geq 90°$, respectively. In order to facilitate efficient transport of a liquid between different functional parts, inner surfaces of the individual parts should primarily be wettable, preferably with a contact angle $\leq 60°$ such as $\leq 50°$ or $\leq 40°$ or $\leq 30°$ or $\leq 20°$. These wettability values apply for at least one, two, three or four of the inner walls of a microconduit. In the case one or more of the inner walls have a higher water contact angle, for instance by being essentially non-wettable, this can be compensated for by a lower water contact angle for the other inner wall(s). The wettability, in particular in inlet arrangements, should be adapted such that an aqueous liquid will be able to fill up an intended microcavity/microconduit by capillarity (self suction) once the liquid has started to enter the cavity, typically with the inner surfaces being in a dry state. A hydrophilic inner surface in a microchannel structure may comprise one or more local hydrophobic surface breaks in a hydrophilic inner wall, for instance as part of a passive valve, an anti-wicking function, a vent solely functioning as a vent to ambient atmosphere etc. See also WO 99058245 (Gyros AB) and WO 02074438 (Gyros AB), and WO 04103890 (Gyros AB) and WO 04103891 (Gyros AB) for preferred hydrophobic surface breaks.

Liquids that are processed with the innovative microfluidic devices, microchannels structures and units are typically aqueous containing water mixed with a water-miscible solvent that may contain one, two or more water-miscible or water immiscible organic solvents such as lower alcohols (methanol, ethanol, isopropanol, n-propanol, a butanol, a pentanol, etc, ethylene glycol, glycerol and other liquid polyalcohols etc), N,N-dimethyl formamide, dimethyl sulfoxide, acrylonitril, dioxin, lower alkyl polyethers such as dioxane, dimethoxy ethylene etc. Due care is taken in combining plastic material with liquid to be processed such that device is not dissolved, deformed or otherwise broken by the liquid to be processed.

The innovative units, microchannel structures, and microfluidic devices can be used for assays with life sciences, such as receptor-ligand assays like immuno assays, nucleic acid assays, etc, enzyme assays, cell based assays etc. Typical variants of these kinds of assays are described in WO 9955827, WO 0040750, WO 02075312, WO 03093802, WO 2004083108, WO 2004083109, WO 2004106926, WO 2006009506, PCT/SE2005/001887 (corresponding US SN 11/filed Dec. 12, 2006 "Microfluidic Assays and Microfluidic Devices"), PCT/SE2006/000071, PCT/SE2006/000072 etc (all of Gyros AB/Gyros Patent AB) which are hereby incorporated by reference in their entirety.

EXPERIMENTAL PART

The Device Used

The drawings illustrate a microchannel structure comprising all functions of units A-F. The structure has been used for the collection of plasma from whole blood.

Figure 1:
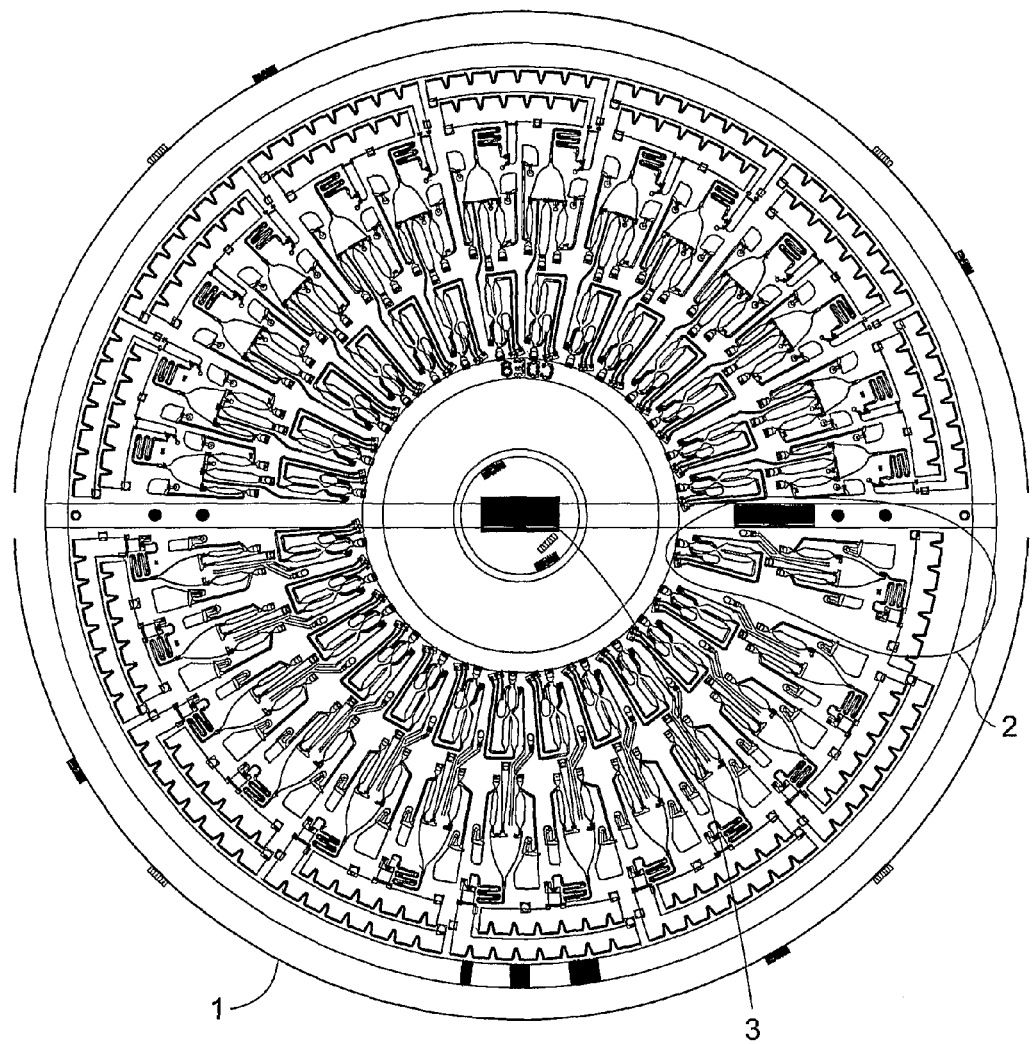
FIG. 1 shows the microfluidic device in which the actual experiments presented below have been carried out.
Figure 2:
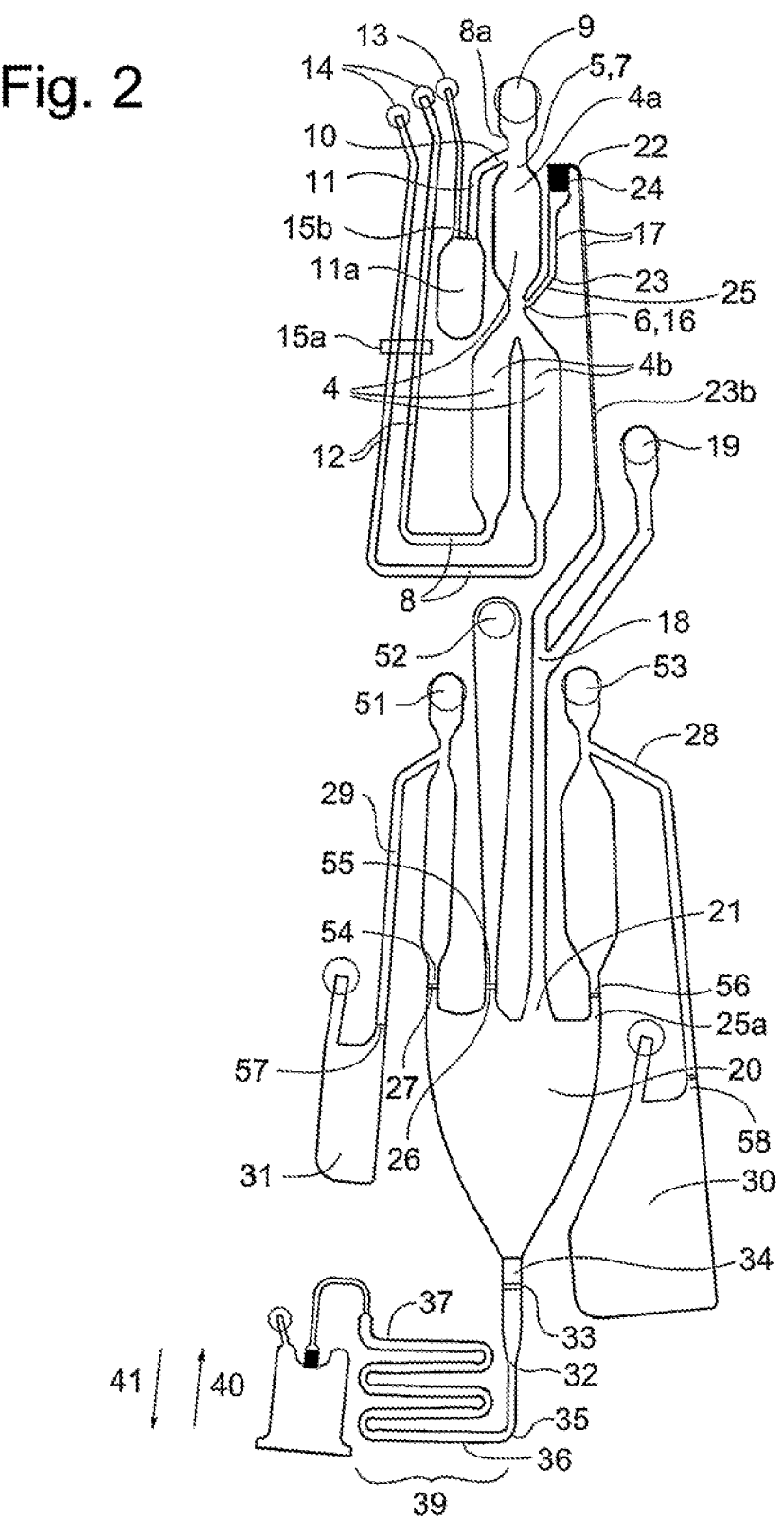
FIG. 2 is an enlarged view of one of the microchannel structures.

The natural size of the device (1) shown in FIG. 1 is the same as a conventional CD having a diameter of 12 cm. From the sizes in FIG. 1 the width of the different parts of the microchannel structures can be concluded bearing in mind that the true diameter is 12 cm.

The depth of the various parts is as a rule 100 µm but may in certain positions be shallower (e.g dual depths/barriers for retaining solid phases in the form of beds of packed particles (columns) (33), microchannels (42) in valve I (24) etc). The device (1) has 27 microchannel structures (2). The device is intended to be spun around a spin axis that passes through the center (3) of the device.

The structure comprises an upstream microcavity I (4a+b) with a liquid inlet I (5) at the top (7)a, a liquid outlet I (6) at an intermediary level between the top (7) and the bottom (8) dividing the upstream microcavity in an upper part (4a) and a lower part (4b). An inlet microconduit (8a) is connected to the liquid inlet I (5) at the top (7) of the upstream microcavity. The inlet microconduit (8a) starts in an inlet port (9) (=Opening in the surface of the device) that is above the level of the top (7) of the upstream microcavity (4a+b). At the same level as the liquid inlet I (5) there is an overflow opening (10) in the inlet microconduit (8a) The overflow opening (10) is connected to a downwardly directed overflow microconduit (11) that brings added excess of liquid (above the overflow opening) down into an overflow microcavity (11a) that vents (13) to the surface of the device (1). The lower/downstream part (4b) of the upstream microcavity (4a+b) divides into two U-shaped finger microconduits (4b) below the level of liquid outlet I (6). The downward part of each finger microconduit narrows/tapers (with angle β) before turning upwards (12).

Each of the upward parts (12) ends in a vent opening (14) in the surface of the device (1) at a level above the level of liquid inlet I (5). The design with U-shaped and tapered finger microconduits is believed to minimize enclosure of air bubbles during filling of the upstream microcavity (4a+b). Valves/vents in the form non-wettable surface areas (15a) (e.g. as finger vents unit C) may be placed in the finger microconduit to minimize the risk for leakage of liquid through the vent openings (13,14) in the surface of the device (1). If these valves/vents are placed below the level of liquid outlet I (6) they are likely to give a more controllable volume-metering in the upper part (4b) of the upstream microcavity (4a+b) and the vent openings (13,14) could also be placed at a lower level than the inlet port (9) and the overflow opening (10) liquid inlet I (5). A non-wettable surface area (15b) (valve) may for similar reasons be placed in the overflow microconduit (11), such as at its connection to the overflow microcavity (11a).

Figure 3:
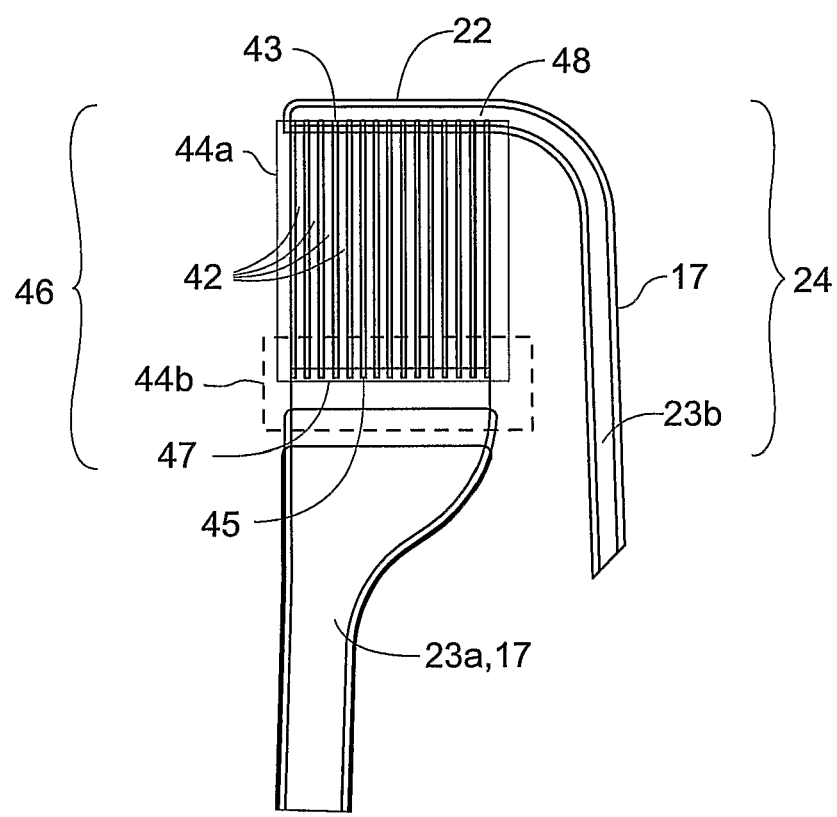
FIG. 3 shows an enlarged view of the key part of unit C.
Figure 4:
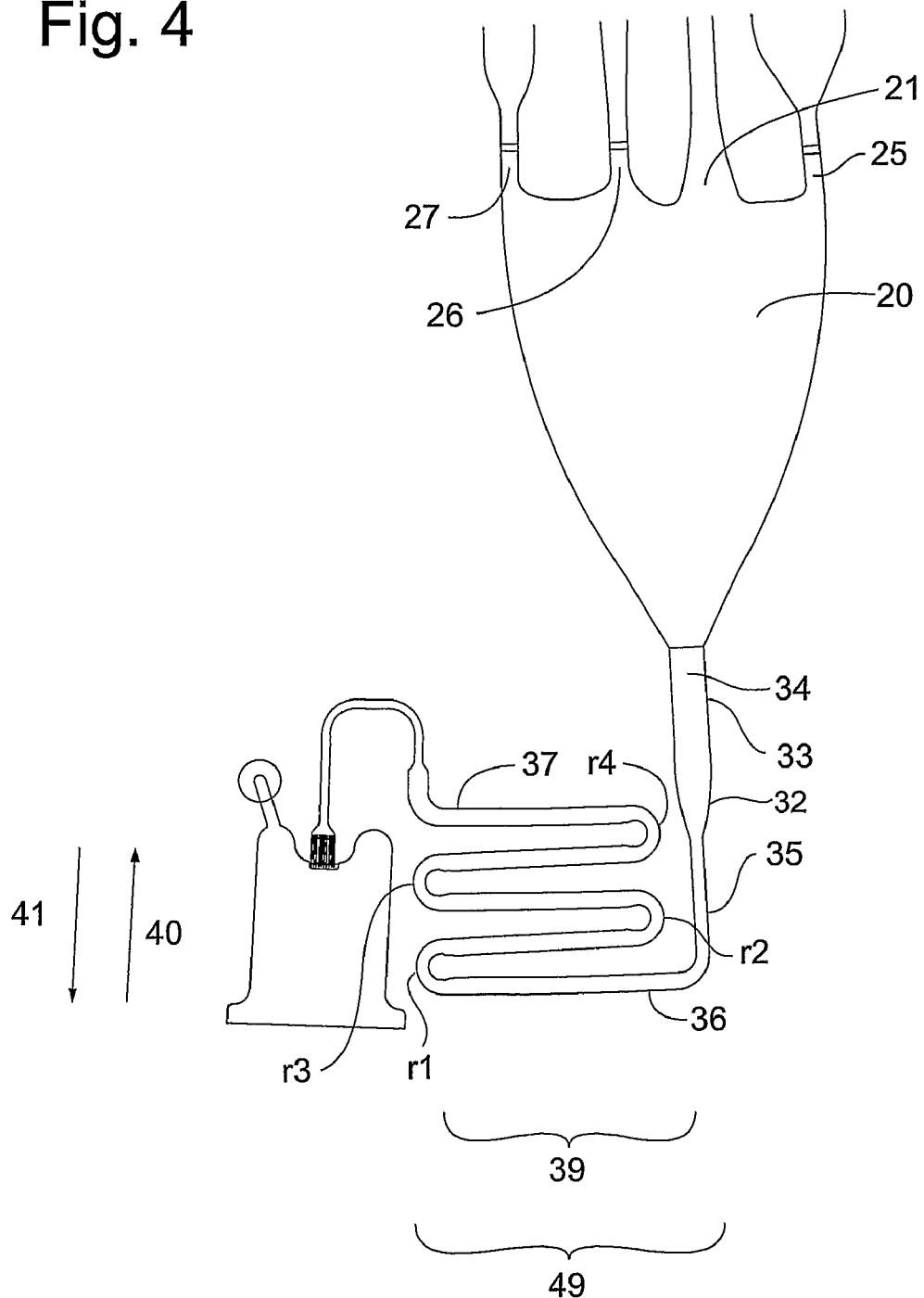
FIG. 4 is the lower part of the structure shown in FIG. 2. The figure focuses on unit F.

Liquid outlet I (6) of the upstream microcavity is connected to the inlet end (16) of microconduit I (17) that ends in an outlet end (18) that is well below the level of the inlet end (16) of the microconduit (level of liquid outlet I (6)). In the structure shown, this outlet end (18) is part of a branching or intersection involving a flow path starting at a liquid inlet function (19) of a downstream microcavity II (20) and ending at a liquid inlet II (21) of this downstream microcavity II (20). The inlet end (16) of microconduit I (17) is at a higher level than the outlet end (18) and has an upward turn with an upper extreme (22). In the upward section (23a) of microconduit I (17) there is a capillary valve I (24) that preferably is a finger valve (unit C) of the type shown in FIG. 3. By varying the position of capillary valve I (24) in microconduit I (17) during the manufacturing of the device, in particular in its upward section (23a), the spin speed required for break through can easily be varied. By adding an extra capillary valve I' (25) (typically as a non-wettable surface break) downstream of capillary valve I (24) advantages as discussed in the specification will be achievable. By placing the upper extreme (22) at a level above the level of the top (7) of the upstream microcavity (4a+b) and capillary valve I (24) at a level below the level of the top (7) there are advantages to gain in the separation of denser material from less dense material in a lower and an upper phase, respectively, as discussed elsewhere in the specification.

The downstream microcavity II (20) may as illustrated in the drawings have a number of liquid inlets II', II'', II''' (25a, 26,27) in addition to liquid inlet II (21). Some of them (25a, 27) may contain a volume-defining unit containing an overflow microconduit (28,29) ending in an overflow microcavity (30,31). In association with liquid outlet II (32) of the downstream microcavity there may be a capillary valve or as in the structure shown means (33,34) for controlling material transport out of the microcavity (20). Thus there may be a barrier (33) constricting the lower part of the microcavity (20) for collecting particles in the form of a particulate solid phase as a packed bed (34) against the barrier (33).

Downstream of the downstream microcavity II (20) there may be a transport microconduit (35) leading to a detection microcavity that is as defined for unit F of the present invention, i.e. the detection microcavity comprises an inlet part (36), an outlet part (37) and a microconduit (39) that defines a meander. As shown in the drawings the meander may have a vertically upward direction (40), i.e. the longitudinal direction of the meander and also the mean flow direction in the meander are in practice fully in the opposite direction to the centrifugal force (41) applied to move the liquid upstream in the meander. The meander has a number of consecutive returns ($r_1$, $r_2$, $r_3$, $r_4$, $r_5$, $r_6$, $r_7$, $r_8$). Within each pair of neighbouring returns ($r_1$, $r_2$; $r_2$, $r_3$; $r_3$, $r_4$; $r_4$, $r_5$ ... ) there is an intermediary section ($r_{1-2}$, $r_{2-3}$, $r_{3-4}$, $r_{4-5}$, $r_{5-6}$, $r_{6-7}$, $r_{7-8}$ ...) that for preferred variants show parallelism for every second section ($r_{1-2}$, $r_{3-4}$, ...) such as for every section ($r_{1-2}$, $r_{2-3}$, $r_{3-4}$, $r_{4-5}$ ...).

The device was manufactured by attaching a lid to a bottom substrate in which the microchannel structures had been replicated by injection moulding (WO 01054810 (Gyros AB)). Before attaching the lid, the surface had been plasma treated (WO 0056808 (Gyros AB)) and local non-wettable surface areas introduced (WO 99058245, WO 04103891 (Gyros AB)). The inner surfaces was subsequently coated with a non-ionic hydrophilic polymer (WO 01047637 (Gyros AB)).

EXPERIMENTAL

Variant A

A microchannel structure (2) containing a separation microcavity (4a+b) (unit E) was used to separate whole blood into cell free plasma. Whole blood was filled into the structure via inlet port (9) to a level above the overflow opening (10). After separation the plasma was delivered down to the column (34) through microconduit I (17) containing a finger valve (24) (units Units A-C) in which the local non-wettable surface (44) fully covers the microchannels (42) of the finger valve (24). During filling of the separation microcavity (4a+b) the front meniscus of the blood will stop at the downstream end of valve I (24).

To separate the blood the following spin sequence was used: (i) 1000 rpm 30 s, (ii) 1500 rpm 180 s, (iii) 4000 rpm 4 s, (iv) 2000 rpm 10 s Steps (i) and (ii) were used to separate the red and white cells from the plasma where the first step also defined the blood volume by activating the overflow microconduit (11). Step (iii) was used to activate the transport of the cell free plasma through capillary valve (24) in microconduit I (17), over the upper extreme (22) and down to the downstream microcavity (reaction microcavity) (20) and to the column (34) and finally step (iv) was used to empty the upper part (plasma chamber) (4b) of the upstream microcavity (4a+b). The cell free plasma was then spun through the column for further processing.

Variant B

If the local non-wettable surface area (44b) is placed across the lower ends (45) or within the of the fingers/micro channels (42) the upper ends (43) of the fingers will be left fully hydrophilic and prone to capillary transport once a liquid front has passed the local non-wettable surface area of the valve. This positioning of the non-wettability permits higher spin speeds and G-forces during the actual separation step (into two phases) and thus also more efficient separations. For instance: (i) 2000 rpm 10 s, (ii) 4000 rpm 50 s, (iii) 9000 rpm 15 s, (iv) 0 rpm 15 s, (v) 2000 rpm 10 s. The spin speeds 2000 to 9000 rpm are used to separate the blood into a plasma fraction and a cell-fraction. At 9000 rpm the plasma breaks the hydrophobic barrier of the valve (24). However, the plasma does not enter the drainage channel until the spin rate is lowered to zero and the capillary force drag in into the drainage channel (downstream/downward section of microconduit I (17)). When the spin rate then increases to 2000 rpm the liquid that has filled the drainage channel will form a driving plug, which will help to empty the plasma chamber.

GENERAL STATEMENT

Certain innovative aspects of the invention are defined in more detail in the appending claims. Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

The invention claimed is:

1. A microfluidic device-comprising a hydrophilic microchannel structure in which there is a functional unit that comprises a microconduit I in which there is an inlet end, an outlet end, and a capillary stop function in the form of a local non-wettable surface area, wherein
    a) the capillary stop function defines a segment of microconduit I,
    b) microconduit I in a part of this segment is divided into two or more microchannels, with at least two of them being functionally equal, and
    c) an inner wall of each of said microchannels is associated with a part of said non-wettable surface area, and
    d) the sum As of the open cross-sectional areas of the microchannels is equal to or larger than the open cross-sectional area immediately before (Ab) and/or after (Aa) the segment, such that the ratio As/Ab or As/Aa is greater than or equal to 1.

2. The device of claim 1, wherein the width and/or depth of each of said microchannels are less than or equal to 0.5 of the corresponding total width and total depth immediately before and/or after the stop function.

3. The device of claim 1, wherein the lengths of each of the microchannel is in the interval $0.1$-$10^5$ times the largest of the width and the depth of the microchannel.

4. The device of claim 1, wherein the microchannels have essentially equal length.

5. The device of claim 1, wherein the segment is
    a) associated with (i) the inlet end of microconduit I, and/or (ii) the outlet end of microconduit I, or
    b) completely within microconduit I.

6. The device of claim 1, wherein the non-wettable surface area
    (i) covers or is abutting a) the inlet ends (upstream ends) of the microchannels, and/or b) the outlet ends (downstream ends) of the microchannels, or
    (ii) is placed within the area between the inlet ends and outlet ends of the microchannels.

7. The device of claim 1, wherein the non-wettable surface area is in at least two parts leaving at least a part of each microchannel between their inlet ends and their outlet ends wettable.

8. The device of claim 1, wherein the capillary stop function is a valve I and microconduit I is for transportation of liquid.

9. The device of claim 1, wherein microconduit I comprises a downstream section, which: a) is downstream of valve I, and b) has a cross-sectional area that is smaller than the cross-sectional area between the inlet end of microconduit I and valve I.

10. The device of claim 1, wherein the outlet end of microconduit I is linked to a liquid inlet II of a downstream microcavity II which comprises:
    a) one or more vent functions, and/or
    b) one or more additional liquid inlets II', II'' . . . at least one of which coincides with one or more vent functions, and/or
    c) one or more liquid outlets II', II'' . . . at least one of which coincides with one or more vent functions, and/or is/are at a lower level than the level(s) of one, two, three or more of said liquid inlets II, II', II'' . . . , and/or
    d) a capillary valve and/or a flow restriction for each of at least one or more liquid outlets II, II', II'' . . . , each of which valve and/or flow restriction is capable of controlling the transport of material through its liquid outlet.

11. The device of claim 10, wherein
    a) the inlet end and the outlet end of microconduit I are directly connected to an upstream microcavity and the downstream microcavity, respectively, and
    b) the segment encompasses the two ends,
each of said microcavities comprising one, two, three or more liquid inlets.

12. The device of claim 8, wherein the device is spinnable about a spin axis to create centrifugal force for driving liquid across said capillary stop function, possibly combined with hydrostatic force created within the microchannel structure by the centrifugal force.

13. The device of claim 12, wherein the inlet end of microconduit I is above the level of the outlet end.

14. The device of claim 1, wherein said capillary stop function is a capillary vent in gas communication with ambient atmosphere.

15. A microfluidic device comprising a hydrophilic microchannel structure in which there is a functional unit that comprises a microconduit I in which there is an inlet end, an outlet end, and a capillary stop function in the form of a local non-wettable surface area, wherein
    a) the capillary stop function defines a segment of microconduit I,
    b) microconduit I in a part of this segment is divided into two or more microchannels, with at least two of them being functionally equal, and
    c) an inner wall of each of said microchannels is associated with a part of said non-wettable surface area,
    d) the capillary stop function is a valve I and microconduit I is for transportation of liquid,
    e) the outlet ends of the microchannels coincide with the outlet end of microconduit I and with the downstream end of the segment,
    f) the non-wettable surface area covers or is abutting from upstream of the inlet ends but not the outlet ends of the microchannels, and
    g) a liquid providing means is connected to the outlet ends of the microchannels.

16. A microfluidic device comprising a hydrophilic microchannel structure in which there is a functional unit that comprises a microconduit I in which there is an inlet end, an outlet end, and a capillary stop function in the form of a local non-wettable surface area, wherein a) the capillary stop function defines a segment of microconduit I,
b) microconduit I in a part of this segment is divided into two or more microchannels, with at least two of them being functionally equal, and
c) an inner wall of each of said microchannels is associated with a part of said non-wettable surface area,
d) the capillary stop function is a valve I and microconduit I is for transportation of
e) the device is spinnable about a spin axis to create centrifugal force for driving liquid across said capillary stop function and
f) microconduit I comprises an upward turn that comprises an upper extreme that is at or above the level of the inlet end of microconduit I.

17. The device of claim 16, wherein said upper extreme is
(i) above the level of upper liquid level I, such as above the level of the uppermost part of the upstream microcavity, or
(ii) at an intermediary level between the level of liquid outlet I and the level of the uppermost part of the upstream microcavity, such as below the level of upper liquid level I of the upstream microcavity,
(iii) at the same level as the inlet end of microconduit I, preferably at the same level as the inlet end/liquid outlet.

18. The device of claim 17, wherein valve I is placed upstream of, downstream of or at said extreme.

19. The device of claim 16, wherein valve I is placed at same level as or above the level of the inlet end/liquid outlet I.

20. The device of claim 14, wherein said part is a microconduit or a microcavity.

21. The device of claim 14, wherein the device is spinnable about a spin axis to create centrifugal force for driving transportation of liquid within the microchannel structures of the device.

* * * * *

UNITED STATES PATENT AND TRADEMARK OFFICE
CERTIFICATE OF CORRECTION

PATENT NO. : 7,947,235 B2  
APPLICATION NO. : 11/911414  
DATED : May 24, 2011  
INVENTOR(S) : Per Andersson et al.

Page 1 of 1

It is certified that error appears in the above-identified patent and that said Letters Patent is hereby corrected as shown below:

Col. 41, Claim 16, line 9, insert --liquid-- after "is for transportation of"

Signed and Sealed this  
Eighteenth Day of October, 2011

David J. Kappos  
*Director of the United States Patent and Trademark Office*